United States Patent
Crockatt et al.

(10) Patent No.: US 10,562,875 B2
(45) Date of Patent: Feb. 18, 2020

(54) AROMATIC COMPOUNDS FROM FURANICS

(71) Applicant: Nederlandse Organisatie voor toegepast-natuurwetenschappelijk onderzoek TNO, 's-Gravenhage (NL)

(72) Inventors: Marc Crockatt, 's-Gravenhage (NL); Jan Harm Urbanus, 's-Gravenhage (NL)

(73) Assignee: Nederlandse Organisaite Voor Toegepast-Natuurwetenschappelijk Onderzoek TNO, 's-Gravenhage (NL)

( * ) Notice: Subject to any disclaimer, the term of this patent is extended or adjusted under 35 U.S.C. 154(b) by 0 days.

(21) Appl. No.: 16/079,751

(22) PCT Filed: Feb. 27, 2017

(86) PCT No.: PCT/NL2017/050121
§ 371 (c)(1),
(2) Date: Aug. 24, 2018

(87) PCT Pub. No.: WO2017/146581
PCT Pub. Date: Aug. 31, 2017

(65) Prior Publication Data
US 2019/0023678 A1    Jan. 24, 2019

(30) Foreign Application Priority Data

Feb. 26, 2016   (EP) .................................... 16157731
Feb. 23, 2017   (EP) .................................... 17157705

(51) Int. Cl.

| | |
|---|---|
| C07D 307/89 | (2006.01) |
| C07C 37/56 | (2006.01) |
| C07C 45/51 | (2006.01) |
| C07C 249/12 | (2006.01) |
| C07C 249/16 | (2006.01) |
| C07C 51/27 | (2006.01) |
| C07D 307/52 | (2006.01) |
| C07C 39/04 | (2006.01) |
| C07C 47/54 | (2006.01) |
| C07C 63/307 | (2006.01) |
| C07C 251/48 | (2006.01) |
| C07C 251/86 | (2006.01) |
| C07B 37/12 | (2006.01) |

(52) U.S. Cl.
CPC ............ *C07D 307/89* (2013.01); *C07C 37/56* (2013.01); *C07C 39/04* (2013.01); *C07C 45/516* (2013.01); *C07C 47/54* (2013.01); *C07C 51/27* (2013.01); *C07C 63/307* (2013.01); *C07C 249/12* (2013.01); *C07C 249/16* (2013.01); *C07C 251/48* (2013.01); *C07C 251/86* (2013.01); *C07D 307/52* (2013.01); *C07B 37/12* (2013.01)

(58) Field of Classification Search
CPC ..................................................... C07D 307/89
USPC ........................................................ 549/247
See application file for complete search history.

(56) References Cited

U.S. PATENT DOCUMENTS

| | | | |
|---|---|---|---|
| 3,962,350 | A | 6/1976 | Horlenko et al. |
| 2014/0142279 | A1 | 5/2014 | Lalezari et al. |
| 2014/0364631 | A1 | 12/2014 | Davis et al. |

FOREIGN PATENT DOCUMENTS

| | | |
|---|---|---|
| WO | WO 2007/136640 A1 | 11/2007 |
| WO | WO 2007/146636 A1 | 12/2007 |
| WO | WO 2014/043468 A1 | 3/2014 |
| WO | WO 2014/064070 A1 | 5/2014 |

OTHER PUBLICATIONS

Higson et al., "Chemical cascades in water for the synthesis of functionalized aromatics from furfurals," Green Chemistry, 2016, 18(7), 1855-1858.
Jacques et al., "Differentiation of anti-inflammatory and anti-tumorigenic properties of stabilized enantiomers of thalidomide analogs", Proc. Natl. Acad. Sci. USA, 2015, 12, E1471-1479.
MacNevin et al., "Stereoselective Synthesis of Quaternary Center Bearing Azetines and Their β-Amino Acid Derivatives", J. Org. Chem., 2008, 73, 1264-1269.
Matsumoto et al., "Acid-catalyzed oxidation of benzaldehydes to phenols by hydrogen peroxide", J. Org. Chem., 1984, 49(24), 4740-4741.
Potts et al., "Furfural Dimethylhydrazone: A Versatile Diene for Arene Cycloaromatization", J. Org. Chem., 1984, 49, 4099-4101.
Potts et al. "Furan-2-carboxyaldehyde N,N-dimethylhydrazones in Diels-Alder cycloadditions", J. Org. Chem., 53(6), 1988, 1199-1202.
Thiyagarajan et al., "A Facile Solid-Phase Route to Renewable Aromatic Chemicals from Biobased Furanics", Angew. Chem. Int. Ed., 2016, 55m 1368-1371.

*Primary Examiner* — Taofiq A Solola
(74) *Attorney, Agent, or Firm* — BakerHostetler

(57) ABSTRACT

Described are methods for preparing phenols, benzene carboxylic acids, esters and anhydrides thereof from furanic compounds by reaction with a dienophile, wherein the furanic compounds are reacted with a hydrazine and/or oxime and then reacted with a dienophile.

19 Claims, 4 Drawing Sheets

AROMATIC COMPOUNDS FROM FURANICS

CROSS-REFERENCE TO RELATED APPLICATIONS

This application is the National Stage of International Patent Application No. PCT/NL2017/050121, filed Feb. 27, 2017, which claims priority from European Patent Application No. 16157731.7, filed Feb. 26, 2016 and European Patent Application No. 17157705.9, filed Feb. 23, 2017, the disclosures of each of which are incorporated herein by reference in their entireties for any and all purposes.

FIELD OF THE INVENTION

The present invention relates to the production of phenols or benzene carboxylic acids, especially from renewable biomass.

BACKGROUND

Aromatic compounds such as phenols and benzene carboxylic acids find many applications in the chemical industry. Benzene dicarboxylic acids and their derivatives, e.g. ortho-phthalic acid (also referred to herein as phthalic acid), meta-phthalic acid (also referred to herein as isophthalic acid) and para-phthalic acid (also referred to herein as terephthalic acid) and their esters, are for instance used on large scale for the production of plasticizers, synthetic fibers, (plastic) bottles, in particular PET bottles, fire-retardant materials, (polyester) resins and the like. Phenols are used as raw materials and additives for industrial purposes in for instance laboratory processes, chemical industry, chemical engineering processes, wood processing, plastics processing and production of polycarbonates. Currently, commercialized processes for the preparation of phenols and benzene dicarboxylic acids typically involve the oxidation of hydrocarbons that are based on fossil fuels such as cumene (for phenol) naphtalene or ortho-xylene (for phthalic acid), m-xylene (for isophthalic acid) and p-xylene (for terephthalic acid).

It is desirable that the production processes of phenols and benzene carboxylic acids, such as respectively phenol, benzene dicarboxylic acids and tricarboxylic acids such as hemimellitic and trimellitic acid/anhydride, that are currently based on using chemicals from fossil feedstocks are replaced or complemented with bio-based production processes, i.e. processes for which the required chemicals originate from a biomass feedstock. Typically, biomass that is suitable for production of chemicals comprises one or more of the following components: oils, fats, lignin, carbohydrate polymers (e.g. starch, cellulose, hemicellulose, pectin, inulin), sucrose, sugar alcohols (e.g. erythritol).

These components can be converted into building blocks for further processing. For instance, carbohydrates can be converted into furanic compounds that may serve as a starting point for the production of phenols, benzenecarboxylic acids and phthalic acids.

A current research aim is providing a process for the large-scale production of phenols or benzene carboxylic acids from renewable feedstock, in particular from lignocellulose-based materials. A first step may be breaking down biomass into lignin, cellulose and hemicellulose, followed by e.g. hydrolysis of the cellulose and dehydration of the obtained sugar to provide furanic compounds. The catalytic dehydration of in particular $C_5$ sugars generally yields furfural and catalytic dehydration of $C_6$ sugars may yield 5-hydroxymethylfurfural (also known as 5-(hydroxymethyl)-2-furaldehyde or 5-HMF) or 5-methoxymethylfurfural (also known as 5-(methoxymethyl)-2-furaldehyde or 5-MMF).

The presence of an electron-withdrawing aldehyde group deactivates the furanic compounds for Diels-Alder (DA) reactions such that harsh reaction conditions are typically required. Due to the harsh conditions and also because furfural and 5-HMF are unstable, furfural and 5-HMF tend to easily decompose or polymerize during the reaction procedure. These furanics are therefore typically unsuitable for direct application in Diels-Alder reactions. As such, furanics comprising an electron-withdrawing group are typically first converted to furanics comprising electron-neutral or electron-donating groups (e.g. by decarbonylation of furfural to furan, hydrogenation of furfural to 2-methylfuran (2-MF) and the like) such that they will be more reactive in Diels-Alders reactions and less harsh conditions are required. However, this approach is generally not desired since this brings additional reduction steps prior to, and oxidation steps after, the Diels-Alder reaction.

A reaction of 2-MF and maleic anhydride (MA) is shown in Scheme 1 in *Angew. Chem. Int. Ed.* 2016, 55, 1368-1371. An intermediate hydrogenation step of the oxabicyclic adduct is used, wherein $H_2$ is consumed to give a hydrogenated DA adduct that is aromatized in a tandem catalytic reaction. However, the latter reaction is aselective and yields a complex mixture of products, and the formation of monoacids is atom inefficient. Further oxidation of the still present methyl group into a carboxyl group would generally require harsh conditions, as mentioned. It would also involve introducing oxygen atoms, in for instance an AMOCO-type process, from an external source, thereby incurring additional costs.

Another approach to obtain benzene carboxylic acids is decarbonylation of furfural to furan (as mentioned in for example WO 2014/064070), followed by a Diels Alder reaction with MA (as described for example in U.S. 2014/0142279) to give the oxabicyclic adduct, followed by ring opening and dehydration to phthalic acid/anhydride. This reaction is not atom efficient; in particular in the decarbonlylation step where a carbon atom and an oxygen atom are lost. It has limited yield because the oxabicyclic Diels-Alder adduct is susceptible to retro-reaction. This yields furan which is not sufficiently stable to the ring opening/dehydration conditions and thus decomposes. The oxabicyclic adduct can also be hydrogenated and aromatized, as described in *Angew. Chem. Int. Ed.* 2016, 55, 1368-1371, but the reaction yields a complex mixture of products of which only about 57% is aromatic. Moreover, this reaction involves the same disadvantage that the process comprises hydrogenation and dehydrogenation.

A reaction of furfural-dimethylhydrazone with MA is described in WO 2007/136640, wherein the formed isobenzofuran is further reacted with 3-aminopiperidine-2,6-dione hydrochloride. The reaction is also mentioned in PNAS 112(12) E1471-1479 for the preparation of thalidomide analogues, wherein it is followed by a reaction with rac-3-amino-2,3-dioxopiperidine. The reaction is also mentioned in *J. Org. Chem.* 49(21) 4099-4101 (1984) and *J. Org. Chem.* 53(6) 1199-1202 (1988). None of these documents is directed to biomass-derived compounds and the conversion of an aldehyde group of a furanic compound into a hydroxyl, carboxylic group or ester group, to provide phenols, benzene carboxylic acids and/or esters thereof. These are generally bulk chemicals.

Particularly desirable is the production of terephthalic acid from renewable biomass. A process for the production thereof from 2,5-dimethylfuran is given in WO 2014/043468.

The production of phenol or bisphenols is also particularly desirable.

DETAILED DESCRIPTION

Figure 1:
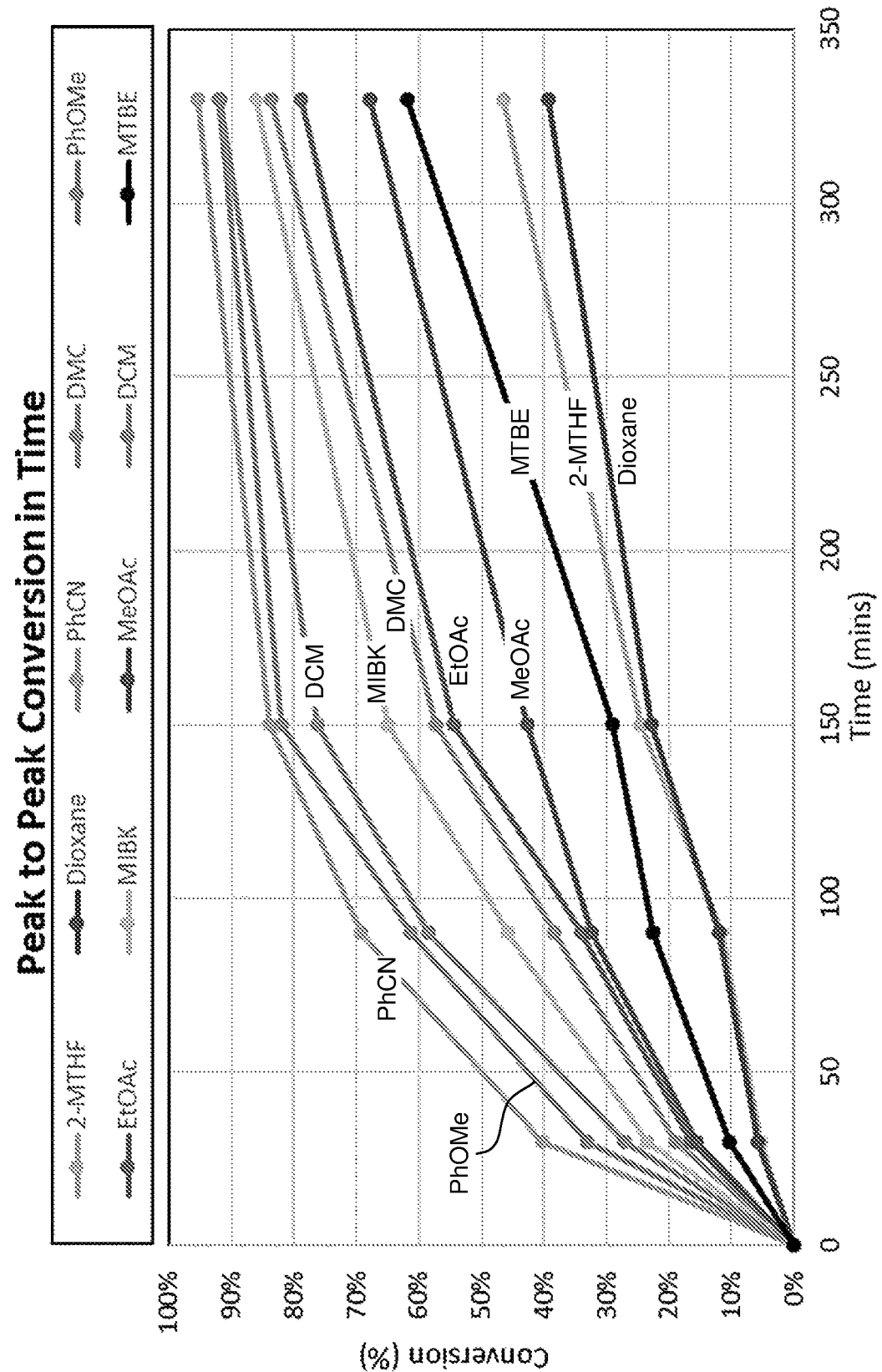
FIG. 1 is a line graph of the peak to peak conversion in time for the various solvents tested in Example 25.

An object of the invention is to provide a method for the production of phenolic or benzene carboxylic acid compounds, and esters thereof from biomass-derived furanic compounds that, for example, is more atom efficient, involves fewer process steps, and may have higher selectivity and yield, and allows for use of relatively inexpensive catalysts.

It was surprisingly found that one or more of these advantages can be achieved at least in part by converting the aldehyde group of a furan carbaldehyde into a hydrazone or oxime group and reacting the hydrazone or oxime compound with a dienophile to give an aromatic compound, suitably followed by conversion of the hydrazone or oxime group in to a hydroxyl, carboxylic acid or ester group by e.g. hydrolysis and oxidation.

In an aspect, the present invention relates to:
A method of preparing a compound having a backbone structure according to formula (I),

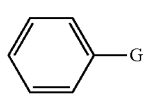

(I)

wherein G is OH, CHO or $CO_2H$, or esters or anhydrides thereof from biomass-derived compounds, comprising reacting a biomass-derived compound having a backbone structure according to formula (II):

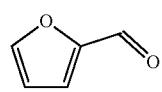

(II)

with a compound with formula (III):

(III)

wherein X is O and z is 0, or X is N and z is 1,
wherein $R_1$ and $R_2$ are each independently an optionally substituted and/or heteroatom-containing hydrocarbyl group or a link to a heterogeneous support, and
$R_2$ can also be hydrogen,
to give a compound with a backbone structure according to formula (IV):

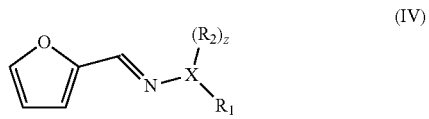

(IV)

and reacting the compound with a backbone structure according to formula (IV) with a dienophile to give a compound with a backbone structure according to formula (V):

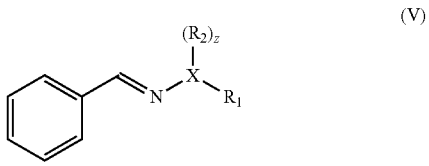

(V)

and converting said compound into the compound of formula (I) by hydrolysis to yield the compound of formula (I) wherein G is CHO (i.e. and aldehyde), and optionally further by oxidation to yield the compound of formula (I) wherein G is OH (i.e. a phenol) or by oxidation to yield the compound of formula (I) wherein G is $CO_2H$ (i.e. a carboxylic acid).

Hence, the method involves, in an aspect, preparing a phenolic or benzene carboxylic compound, or esters thereof, from a furan carbaldehyde, by condensation of the aldehyde group on the furanic ring with a hydrazine compound or a hydroxylamine, to provide the corresponding hydrazone or oxime group on the furanic ring, and reacting the hydrazone or oxime furanic compound with a dienophile, to form an aromatic hydrazone or oxime, suitably through ring opening of a bicyclic adduct as intermediate, and conversion of the hydrazone or oxime to give the corresponding phenol, carboxylic acid or ester thereof, through hydrolysis and oxidation. For example, the hydrazone or oxime is hydrolysed to the corresponding benzaldehyde, followed by oxidation of the aldehyde group into carboxylic acid and/or hydroxyl. When carboxylic acid is obtained, the carbonyl carbon atom of the furan carbaldehyde is maintained in the obtained benzene carboxylic acid. Advantageously, the atom efficiency of the reaction with furfural-hydrazones and ethylene to obtain phenol is the same as for the reaction of furan with acetylene.

Advantageously, by converting the aldehyde group into a hydrazone or oxime group, the oxidation state of the carbon atom of the aldehyde group is not altered while elegantly the hydrazone or oxime group is electron-donating, thereby rendering the furan more reactive for DA reactions. In particular, the second heteroatom (X in formula III) suitably has a lone pair of electrons that has p-orbital overlap with the furan ring, for instance through resonance interaction. Providing the hydrazone or oxime group may result in an increase of the HOMO (highest occupied molecular orbital) energy of the furan ring, relative to that of e.g. furfural. In this way, the reaction with the dienophile and ring opening may be enabled or promoted, and the aldehyde functionality can be restored in the aromatic product without oxidation, using for example hydrolysis. A further oxidation of the aldehyde to hydroxyl or carboxylic acid can be relatively mild, and likewise oxidation of a hemiacetal to ester. This can be contrasted by the harsh conditions necessary for oxidation of a methyl group into carboxylic acid, if for instance a methylfuran compound was subjected to Diels-Alder reaction.

The compound that is reacted with the compound with formula (III) is a furanic compound with formula (II), for example a furan carbaldehyde, that is for instance biomass derived.

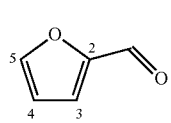
(II)

The furan with formula (II) is optionally substituted at any one or more of the 3, 4 and 5 position, in particular at the 5 position, for example only at the 5 position, for instance with one or more groups independently selected from the group consisting of optionally substituted or heteroatom-containing hydrocarbonyl, for example a $C_1$-$C_{20}$ hydrocarbonyl, preferably $C_1$-$C_8$, such as linear or branched alkyl, alkenyl, alkynyl, cycloalkyl, aryl, aralkyl and alkaryl, more in particular methyl; and F, Cl, Br, I, —$CH_2F$, —$CH_2Cl$, —$CH_2Br$, —$CH_2I$, —CN, —$NO_2$, —CHO, —$CO_2H$ and esters thereof, —$CH_2NH_2$ and secondary, tertiary and quaternary amines or amides thereof, and —$CH_2OH$ and esters or ethers thereof; wherein said heteroatoms are optionally selected from O, N, S, and P, and wherein said substituents are optionally from the mentioned substituents.

In an embodiment, the compound with formula (II) is optionally substituted with one or more groups independently selected from the group consisting of —$CH_2OR$, —(C=O)R, —(C=O)OR, wherein R is hydrogen or hydrocarbonyl, preferably $C_1$-$C_6$ hydrocarbonyl. Optionally, the compound is only substituted with such groups, for example only at the 5 position, or is obtained from such compound. Optionally, a mixture of compounds with formula (II) is used.

Hence, the method uses an optionally substituted furan-2-carbaldehyde. For example, the method uses furfural, furan-2,5-dicarbaldehyde (DFF), 5-hydroxy-methylfurfural, 5-methoxymethylfurfural or 5-chloromethylfurfural, or a mixture thereof since these compounds can be obtained from $C_5$ and/or $C_6$ sugars under acidic conditions. In such case, the method may comprise an optional step of providing these compounds with one or more substituents, and subsequent reaction with the compound with formula (III).

Preferably, the compound with formula (II) is biomass-derived, more preferably derived from $C_5$ and $C_6$ sugars obtained from renewable biomass. Optionally, the method comprises preparing a compound with formula (II) from sugars and/or from biomass. The biomass may for instance comprise one or more of the following components: oils, fats, lignin, carbohydrate polymers (e.g. starch, cellulose, hemicellulose, pectin, inulin), sucrose, sugar alcohols (e.g. erythritol).

The method may comprise converting the biomass into furanics for example in a one or a two-step procedure. In a two-step procedure biomass is typically first pre-treated to hydrolyse the cellulose and hemicellulose in order to obtain free sugars, i.e. non-polymerized sugars. This hydrolysis can be conducted by means of enzymatic fermentation, acid catalysis, and the like. Said sugars are then converted in a separate step into one or more furanics by means of acid-catalysed dehydrations. The method may also optionally comprise dehydration of sugars to yield furan derivatives such as furfural and 5-HMF, for example as described in WO 2007/146636, or converting cellulose and hemicellulose directly into one or more furanics by acid-catalysis. Given the limited variety of sugar units in biomass, only a limited variety of furanics are obtained directly from biomass. Therefore, in the present invention the variety of furanics is also limited in some embodiments. Typically, 5-HMF or 5-MMF is obtained from cellulose and furfural is obtained from hemicellulose.

The compound with formula (II) may also be obtained from other sources than biomass, such as from petrochemical processes or for example from carbohydrate-containing waste streams.

In the method, the compound with formula (II) is reacted with a compound with formula (III):

(III)

wherein X is O and z is 0 or X is N and z is 1,
wherein $R_1$ and $R_2$ are each independently an optionally substituted and/or optionally heteroatom-containing hydrocarbyl group, or a link to a heterogeneous support and $R_2$ can also be hydrogen.

Preferably, $R_1$ is such that the heteroatom X is attached to a $sp^3$ or $sp^2$ hybridized carbon, and $R_2$, if present, is preferably either hydrogen or is attached to the heteroatom X by a $sp^3$ or $sp^2$ hybridized carbon. X more preferably has only single bonds with $R_1$ and, if present, $R_2$. Lack of conjugation of X with $R_1$ and $R_2$ may contribute to the activation of the furanic ring for Diels-Alder reactions.

$R_1$ and $R_2$ are for example independently an unsubstituted or substituted $C_1$-$C_{20}$ or $C_1$-$C_{12}$ hydrocarbyl, or for instance each $C_4$-$C_{12}$ hydrocarbyl, for example a $C_1$-$C_{12}$ linear or branched alkyl or $C_3$-$C_8$ cycloalkyl, and may also be joined to form a ring, wherein the optional substituents are for example selected from the group consisting of phenyl and F, Cl, Br, I, —$CH_2F$, —$CH_2Cl$, —$CH_2Br$, —$CH_2I$, —CN, —$NO_2$, —CHO, —$CO_2H$ and esters thereof, —$CH_2NH_2$ and secondary, tertiary and quaternary amines or amides thereof, and —$CH_2OH$ and esters or ethers thereof, and —O—, wherein said ethers, esters and amides for example $C_1$-$C_6$ alkyl ethers, esters and amides.

Hence, the compound with formula (III) is for instance an O-substituted hydroxylamine or an 1,1-disubstituted hydrazine Preferably, the X is N and $R_1$ and $R_2$ are each, independently, linear or branched $C_1$-$C_8$, such as $C_1$-$C_4$ alkyl, e.g. methyl, ethyl, n-propyl, isopropyl, cyclopropyl, n-butyl, sec-butyl, isobutyl, or tert-butyl. For example, the compound with formula (III) is 1,1-dimethylhydrazine. Also possible is that $R_1$ and/or $R_2$ is an optionally substituted phenyl or benzyl, wherein the optional substituents are for example selected from the group consisting of halogen, $C_1$-$C_4$ alkyl and —$NH_2$ or —OH, which may both be optionally substituted with one or two $C_1$-$C_5$ (cyclo-)alkyl.

In an embodiment, the compound with formula (III) is supported on a heterogeneous support, for example a solid support, such as a polymer support, to allow for easier recovery of the hydrazine Polymer-supported and resin-supported hydrazine reagents are known as such, for example in the form of beads.

The reaction may be conducted for instance in an appropriate reaction vessel at room temperature, optionally in the presence of a drying agent and optionally in a solvent.

The reaction product has for example a backbone structure having formula (IV), with X, $R_1$ and $R_2$ as for formula (III):

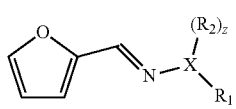
(IV)

The compound with formula (IV) is a hydrazone or oxime compound and is reacted with a dienophile.

Hence, in a preferred embodiment the compound with formula (IV) has for example the formula:

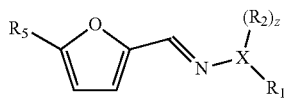

wherein $R_5$ is an optionally substituted and/or heteroatom-containing hydrocarbyl group, as specified for formula (II), and is preferably selected from the group consisting of —CH=N—X($R_1$)($R_2$)$_z$, —$CH_2OR_6$, —(C=O)$R_6$, —(C=O)O$R_6$, wherein $R_6$ is hydrogen or hydrocarbonyl, preferably $C_1$-$C_6$ hydrocarbonyl.

Advantageously, the reaction of the compound with formula (IV) with a dienophile is not or less liable to retro-reaction, and/or more liable to ring-opening and aromatization, by virtue of the hydrazone or oxime group, thereby allowing the reaction to be driven to higher yield. Optionally, the compound with formula (IV) is obtained and collected as intermediate product, for example by purification, for instance by distillation and/or crystallization.

The dienophile is for example an alkene or an alkyne. The dienophile may suitably have electron withdrawing groups at one or both sides of the acetylene or ethene moiety. The dienophile may for instance have a formula (VI):

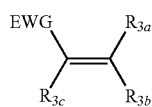
VIa

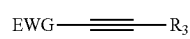
VIb wherein EWG is an electron-withdrawing group and $R_3$=H, linear or branched $C_1$-$C_8$-alkyl, or EWG, and $R_{3a}$, $R_{3b}$ and $R_{3c}$ are for example, independently, EWG, H, $C_1$-$C_8$ saturated hydrocarbyl, such as alkyl or $C_3$-$C_8$ cycloalkyl, and are optionally substituted, for example only with one or more EWG as substituent; and wherein optionally at least two of EWG, $R_{3a}$, $R_{3b}$ and $R_{3c}$ are joined to form a ring. In a preferred embodiment, any and all heteroatoms in the dienophile are provided as part of an EWG.

More preferably EWG=—CN, —$NO_2$, —$CO_2X$, —C(O)NX, —C(=NY)X, —$CF_3$, —$CCL$, —$CBr_3$, —CL, —$SO_2X$, —$SO_3X$, —COH, —COX, —COF, —COCl, —COBr, —COI, wherein X and Y are independently H, or $C_1$-$C_8$ hydrocarbyl, in particular a linear or branched alkyl or cycloalkyl, optionally substituted with halogens. The dienophile is optionally polymer-supported. However, if the compound with formula (III) is provided on a heterogeneous support, then preferably the dienophile is not supported and is preferably provided as dissolved in the reaction medium.

Alkene dienophiles common in the art may be used, for instance selected from the group consisting of acrylonitrile, maleic anhydride, maleimides, methyl acrylate, 2,2,2-trifluoroethyl acylate, 1,1,1,3,3,3-hexafluoroisopropyl acrylate, citraconimide, dimethyl acetylenedicarboxylate, acetylene dicarboxylic acid, 3-buten-2-one, 1,4-benzoquinone, allyl chloride, maleic acid, fumaric acid, itaconic acid, aconitic acid, acrylic acid, crotonic acid, isocrotonic acid, methacrylic acid, tiglic acid, vinyl acetate, and esters of maleic and fumaric acids, for example dimethyl maleate and dimethyl fumarate, and alkyl esters of any of such acids. Use of an ester as dienophile, such as with formula (VIa) or (VIb) wherein $R_3$ is —$CO_2X$, wherein X is preferably linear or branched $C_1$-$C_8$ alkyl, in particular in combination with a Lewis acid catalyst, may be useful to avoid possible interactions between the compound with formula (III) and carboxylic acids.

In some embodiments, the dienophile is an alkene, for example having formula (VI), and the double bond which reacts with the furanic compound with formula (IV) is not part of a ring.

In some embodiments, the dienophile is an alkene with formula (VIa), wherein EWG is —$CO_2X$, wherein X is H, or linear or branched $C_1$-$C_8$ alkyl, preferably wherein X is linear or branched $C_1$-$C_8$ alkyl, optionally substituted with halogens and optionally polymer-supported, and wherein preferably $R_{3a}$, $R_{3b}$ and $R_{3c}$ are selected from hydrogen, methyl and ethyl, or —$CO_2X$ with X as defined for EWG. More preferably, the dienophile is (meth)acrylic acid or alkyl (meth)acrylate. Advantageously, if the dienophile is acrylic acid or acrylate, only a carboxyl group or carboxylate group is introduced into the formed aromatic compound. With furfural as compound with formula (II) and acrylic acid as dienophile, phthalic acid and isophthalic acid may be obtained. With 5-HMF or 5-MMF and acrylic acid, for example trimellitic acid may be obtained.

The dienophile may also be a carboxylic acid, wherein EWG is —$CO_2X$, preferably with a vinyl group. If a carboxylic acid such as maleic acid or a derivative thereof (e.g. maleic anhydride) is used as dienophile, then for example N,N-dimethylhydrazine can be used with for instance furfural and advantageously no drying agent is necessary and/or no solvent is used. If a solvent is used, this may contain water. Suitable solvents include, for example, 2-methyltetrahydrofuran, anisole, dimethyl carbonate, 1,4-dioxane, ethyl acetate, methyl acetate, methyl isobutylketone and benzonitrile, dichloromethane, methyl t-butylether, toluene and 2-sec-butylphenol. Also possible is to run the reaction neat, for instance if the reaction comprises combining furfural with a hydrazine such as N,N-dimethylhydrazine.

In some attractive embodiments, the dienophile is a compound with formula (VIc):

(VIc)

wherein Q is selected from the group consisting of O, N, S, or P, more preferably O; and $X_1$ and $X_2$ are independently a —($CH_2$)—, —(C═O)—, —(HCOY)— or —(C(OY)$_2$)—, preferably —($CH_2$)— or —(C═O)—; and Y is independently a hydrogen, linear or branched $C_1$-$C_4$ hydrocarbyl. Preferably, the dienophile is maleic anhydride. Using a furfural-derived hydrazone and maleic anhydride as dienophile, 3-carboxyphthalic acid/anhydride (also known as 1,2,3-benzenetricarboxylic acid/anhydride or hemimellitic acid/anhydride) may be obtained as product. Using 5-HMF or 5-MMF and maleic anhydride, 3,6-dicarboxyphthalic anhydride or 1,2,3,4-benzenetetracarboxylic acid may be obtained as product after hydrolysis and oxidation.

In a preferred embodiment, the dienophile comprises a but-2-ene-1,4-dione moiety included in a 5- or 6-membered ring and is for example maleic anhydride.

Some factors for the choice of the dienophile include the groups to be introduced into the groups that are desirable or acceptable as substituents on the phenyl moiety of the benzene carboxylic product, and the reactivity of the dienophile.

Also possible is the use of ethylene or acetylene, or more generally an unactivated alkene or alkyne. For example, an alkene or alkyne not comprising an EWG can be used, for instance an unsubstituted $C_2$-$C_{12}$ alkene or alkyne, that is preferably 1,2-unsaturated.

Although ethylene is normally not very reactive for Diels-Alder reactions, the presence of the hydrazone or oxime group on the furanic compound may enable the use of ethylene as dienophile with a variety of catalysts, for instance catalysts similar to those used for the reaction of 2,5-dimethylfuran with ethylene.

In a preferred embodiment, ethylene is used as dienophile. One or more steps of the reaction of the compound with formula (IV) with ethylene, such as the formation of the aromatic compound, may for example be catalysed by a Lewis acid and/or Brønsted acid. For example, a supported, or solid or homogenous Brønsted acid may be used. For instance, a porous solid acid material may be used, such as microporous silica, alumina, or aluminasilicate can be used, for example zeolite, or an activated carbon support. Zeolites for example may provide a combination of Lewis acid and Brønsted acid functionality. The reaction is conducted for instance above 200° C., such as above 250° C.

If an alkyne dienophile is used, this may for instance be a compound selected from the group consisting of:

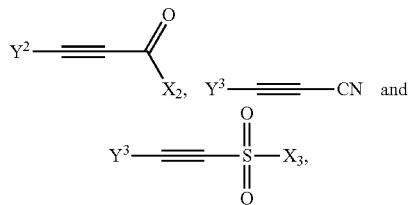

wherein $Y^2$═H, $CH_3$ or $CO_2X_A$ and $X^2$═H, $CH_3$, halogen, $OX_A$ or $NX_AX_B$; $Y^3$═H or $CH_3$, $X^3$═$CH_3$, $OX_A$, $NX_AX_B$ or halogen, $Y^4$═H, $CH_3$, $SO_2X^{3-}$; and $X_A$ and $X_B$ are independently hydrogen or hydrocarbon, for example $C_1$-$C_4$ alkyl.

If the dienophile is an alkyne, a phenolic compound is obtained. With an acetylene derivative according to formula VIb, wherein $R_3$ is hydrogen, a phenolic product is obtained, for instance having the formula (VII):

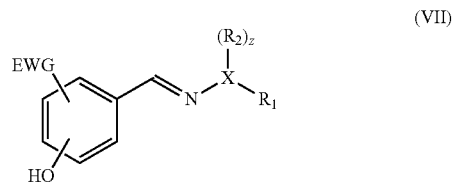

(VII)

for example, with the hydroxyl para to the hydrazone or oxime group. In an advantageous embodiment, the dienophile is an alkyl propiolate, more preferably a linear $C_1$-$C_8$ alkyl propiolate, in particular methyl propiolate, and as such an ester is present as EWG in the compound with formula (VII).

In the present invention, the furanic compound may be considered as a diene. A reaction between a diene and a dienophile is known in the field as a Diels-Alder reaction. As such, for the present invention the reaction of the furanic compound with the dienophile may be referred to as the Diels-Alder reaction. However, it will be appreciated that the present invention is directed to any reaction of the furanic compound with a dienophile, independently of the specific reaction pathway of mechanism involved. For instance, although the Diels-Alder reaction is a concerted reaction, viz. a single-step reaction without any intermediate, a non-concerted reaction such as e.g. a Friedel-Craft-type pathway is also within the scope of the present invention. Without wishing to be bound by way of theory, an oxabicyclic adduct is formed, having a six-membered ring and a ring with a bridging oxygen atom, in addition to any fused ring from the dienophile. The oxygen-bridging ring may undergo ring-opening, usually in situ, for instance if a Lewis or Brønsted acid catalyst is used. The ring opening may also involve a rearrangement, e.g. a hydroxyl- or methyl-migration. The presence of a hydrazone or oxime group during this ring opening may advantageously increase the rate thereof.

In a particular embodiment of the present invention, the Diels-Alder reaction is catalyzed. Preferably the catalyst is a Brønsted acid or a Lewis acid, or a combination thereof, for example an aprotic Lewis acid, optionally supported on or provided by a solid material or a heterogeneous support, for example silica or a polymer. More preferably the catalyst is a Lewis acid based on a metal, preferably a metal selected from the group consisting of Zn, Al, Sc, B, Fe, Ir, In, Hf, Sn, Ti, Yb, Sm, Cr, Co, Ni, Pb, Cu, Ag, Au, Tl, Hg, Pd, Cd, Pt, Rh, Ru, La, Ce, Pr, Nd, Pm, Eu, Gd, Tb, Dy, Ho, Er, Tm, Lu, V, Mn, Y, Zr, Nb, Mo, Ta, W, Re, Os and combinations thereof. Even more preferably, the catalyst is selected from the group consisting of $ZnI_2$, $ZnBr_2$, $ZnCl_2$, $Zn(Ac)_2$, $Sc(OSO_2CF_3)_3$, $Y(OSO_2CF_3)_3$, $AlCl_3$, $Al(Et)_2Cl$, $BCl_3$, $BF_3$, $B(Ac)_3$, $FeCl_3$, $FeBr_3$, $FeCl_2$, $Fe(Ac)_2$, $IrCl_3$, $HfCl_4$, $SnCl_4$, $TiCl_4$, clays, zeolites and combinations thereof. Even more preferably, the catalyst is selected from the group consisting of $ZnI_2$, $ZnBr_2$, $ZnCl_2$, $Sc(OSO_2CF_3)_3$, $Y(OSO_2CF_3)_3$, $AlCl_3$, $Al(Et)_2Cl$, $TiCl_4$ and combinations thereof. The reaction can also be conducted without catalyst. Without wishing to be bound by way of theory, the catalyst may also catalyze the ring-opening of the oxabicyclic adduct, for instance to a ring-opening dehydration reaction.

If a solid and/or solid supported catalyst is used, such as a zeolite, then the compound with formula (III) is suitably dissolved or at least dispersed in a liquid phase of the reaction medium. In such case, the compound with formula (III) is preferably non-volatile and/or contained within the process. For instance, $R_1$ and $R_2$ of the compound with formula (III) may comprise each at least 4 or at least 6 carbon atoms, or at least 8 carbon atoms; or $R_1$ and $R_2$ in total at least 6 or at least 10 or at least 12 carbon atoms.

In a preferred embodiment, the catalyst is a haloacetic acid, such as a fluoroacetic acid or chloroacetic acid. For instance, the catalyst may be a trihalogenated acetic acid. Good results have been obtained using trifluoroacetic acid as catalyst.

The reaction of the compound with formula (IV) with a dienophile can be performed for example at a temperature ranging from −60 to 350° C., preferably −20 to 300° C., more preferably 50 to 280° C. The precise temperature depends on the furanic compound and dienophile used. In some embodiments, the reaction is performed at ambient temperature (e.g. between about 5° C. and about 35° C.), for example using a Brønsted acid catalyst such as trifluoroacetic acid.

The dienophile is for example provided in about 1 equivalent per furanic compound, for example a molar ratio for example in the range 2:1 to 1:2, more instance 1:1 to 1:1.5 of furanic compound to dienophile. The Diels-Alder reaction may be performed for example at a pressure ranging from 0-200 bar, preferably 1 to 100 bar. The Diels-Alder reaction is typically performed in a liquid phase, such as neat, e.g. without solvent, or for example in suitable solvent, preferably in a concentration of 0.1-3 M, more preferably about 2 M, of the furanic compound. The solvent is for instance selected from the group consisting of alcohols, esters, ketones, aliphatic hydrocarbons, aromatic hydrocarbons, organic acids, ethers, diprotic apolar solvents, halogenated solvents, nitrated solvents, ionic liquids, organic bases and combinations thereof.

Suitably, the hydrazone or oxime group is subjected to hydrolysis, to provide the corresponding aldehyde and then, in some embodiments, to oxidation to a carboxylic group. For the hydrolytic cleavage of the carbon-nitrogen bond, the liberated nitrogen base is preferably trapped or removed, to drive the reaction forward, for instance by distillation. The reaction may for instance be performed using an acid which protonates the hydrazine to limit the reverse condensation reaction.

The hydrolysis is for example conducted with excess water and for instance catalyzed, such as by a Brønsted acid and/or Lewis acid, for instance by a weak Brønsted acid, or an aprotic Lewis acid. It may also be carried out in concentrated acids, e.g. concentrated hydrochloric acid. The hydrolysis can be conducted using known methods for hydrolysis of compounds comprising a N═C bond, such as hydrazone and oxime compounds, into the corresponding ketones and aldehydes. In a preferred embodiment, the hydrolysis is carried out biotechnologically, e.g. in an enzymatic process.

With some reagents for the hydrolysis, the oxidation may occur simultaneously. In a preferred embodiment, nitric acid is used for the hydrolysis and/or oxidation. Hence, in a preferred embodiment, the dienophile is maleic anhydride and the compound with a backbone structure according to formula (V) is converted into the product having a backbone structure according to formula (I) in a single step involving hydrolysis and oxidation, using for example nitric acid.

The hydrolysis may for example be conducted using glyoxylic acid and $H_2O$. For instance, 50% aqueous glyoxylic acid (2 mL) per 1 mmol hydrazone may be used at room temperature. The hydrolysis may also be conducted for example using bismuth trichloride/THF, for example with a small amount of water and under microwave irradiation. Yet a further option may be the use of trimethylsilyl chloride and sodium iodide with MeCN. Optionally, the hydrazone or oxime is subjected to hydrolysis using microwave irradiation and an acid, such as a carboxylic acid or a mineral acid, for a period of for example up to 1 hour, up to about 10 minutes or up to about 1 minute.

If the hydrazine or oxime compound with formula III was bonded to a support, this would facilitate the recovery and reuse of the formed hydrazine or hydroxylamine. In a preferred embodiment, the compound with formula (III) is provided on a heterogeneous solid support, and the method comprises recovery of the compound with formula (III) by separation of the solid support material comprising the compound with formula (III) from a liquid phase comprising an aromatic product preferably with formula (I). Separation of magnetic heterogeneous solid supports can for instance be carried out using magnetic fields.

The oxidation of the aldehyde into the corresponding carboxylic acid may be conducted under relatively mild conditions and is known as such in the art. For example, $Ag_2O$ or, potassium peroxymonosulfate could be used. An AMOCO-type process may also be used.

Certain oxidation condition may result in conversion of the aldehyde into hydroxide. For instance, oxidation of aromatic aldehydes by hydroperoxide or peracids (e.g. meta-chloroperoxybenzoic acid, or persulfuric acid) generally readily form the corresponding phenol. Such reactions are respectively also known as the Dakin or Baeyer-Villiger oxidations (see e.g. Matsumoto et al. *J. Org. Chem.* 49, 4740-4741 (1984)).

Phenols may also be obtained from benzaldehydes via benzoic acids as intermediate compound (see e.g. Paul L. Alsters et al. Handbook of Advanced Methods and Processes in Oxidation Catalysis: From Laboratory to Industry 2014, page 408-410 and references therein).

Also possible is oxidation of the aromatic hydrazone to the corresponding nitrile, followed by hydrolysis of the nitrile.

The method of the invention advantageously allows for preparing benzene dicarboxylic acids, such as phthalic acid, isophthalic acid and terephthalic acid. Also, hemi-mellitic and trimellitic acid may be obtained. Generally, for example benzene monocarboxylic acids, such as benzoic acid, benzene dicarboxylic acids, benzene tricarboxylic acids, and benzene tetracarboxylic acids may be obtained, as well as for example hydroxybenzene mono di, tri, and tetra carboxylic acid, as well as esters and anhydrides thereof. In some embodiments, the benzene carboxylic acid has no other substituents than the carboxylic group and optionally the hydroxyl groups.

In addition, the method of the invention advantageously allows for preparing phenols such as phenol as well as hydroxybenzoic acids such as hydroxy tetracarboxylic acids, hydroxyl tricarboxylic acids, hydroxyl dicarboxylic acids, and hydroxyl carboxylic acids. Particularly hydroxybenzoic acids such as 4-hydroxybenzoic acid, 2-hydroxybenzoic acid, 3-hydroxybenzoic acid, 2,4-dihydroxybenzoic acid, 3,4-dihydroxybenzoic acid, 2-hydroxyterephthalic acid, 2-hydroxyisophtalic acid, 3-hydroxy-benzene-1,2,4-tricarboxylic acid, 5-hydroxy-benzene-1,2,4-tricarboxylic acid, 4-hydroxy-benzene-1,2,3-tricarboxylic acid, 5-hydroxy-benzene-1,2,3,4-tetracarboxyilic acid and 4-hydroxy-benzene-1,2,3,5-tetracarboxyilic acid are attainable by the present invention.

The method or at least the reaction with the dienophile may be performed batch-wise or preferably in a continuous process. For a batch process, the reaction is optionally performed as a one pot synthesis, for instance the reaction with the compound with formula (III) and the reaction with the dienophile, by sequential addition of reagents, for example without work-up. This is optionally also possible if the feed containing the compound with backbone structure with formula (II) also comprises water. The feed is for example an effluent from a reactor, for instance from a biphasic reactor, that is optionally filtrated or phase separated to provide an organic phase used as feed for the method of the invention.

Generally, the feed for the method, or for the reaction with the compound with formula (III), that comprises the furanic compound, is for example an effluent from a reactor for the catalytic dehydration of biomass. The feed may comprise an organic solvent and/or water, such as for example obtained from a biphasic reactor. The feed may in particular comprise a mixture of furanic compounds. The furanic can for instance be prepared with super-heated steam, which provides a furanic/water product solution for use in the method according to the present invention.

Optionally, a solid-supported compound with formula (III) is used, wherein the solid material may for example be immobilized. The solid-material comprising the compound with formula (III) may be supplied as particles, powder, or in granular form and is for example a polymer-supported hydrazine or hydroxylamine. The solid supported compound is for example used as a mobile phase and for example passed through a zone for reaction with a dienophile and subsequently through one or more zones for hydrolysis and oxidation, and then recovered and reused, or it may be a stationary phase.

Preferably, the dienophile comprises a vinyl group, and preferably the dienophile is a carboxylic acid. More preferably, the dienophile is acrylic acid or an ester thereof, as it allows for introducing carboxylic groups into the formed aromatic compound.

The dienophile may also be an acrylate ester, preferably an alkyl acrylate ester, for instance with a $C_1$-$C_6$ alkyl group, more in particular methyl acrylate.

If furfural is used and acrylic acid and esters thereof as dienophile, the Diels-Alder reaction may give the following compounds:

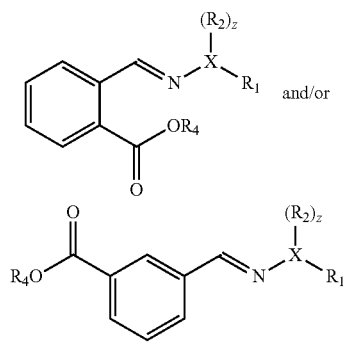

wherein X, $R_1$, $R_2$ and z are as defined before, and $R_4$ is hydrogen or a hydrocarbyl, preferably an alkyl or cycloalkyl with 1 to 6 carbon atoms, and wherein preferably X=N and preferably $R_1$=$R_2$=methyl.

These compounds can be converted into the corresponding dicarboxylic acid using hydrolysis and oxidation of the hydrazone or oxime group, for instance as described above.

In yet a further embodiment, the hydrazone or oxime furanic compound has the formula (VIII), for instance obtained by reacting 5-HMF with the compound with formula (III):

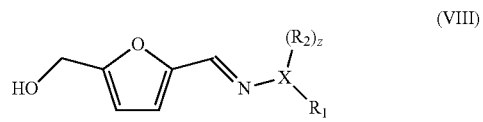

wherein X, $R_1$ and $R_2$, and z are as defined before, and preferably X=N and preferably $R_1$=$R_2$=methyl, and is reacted with acrylic acid and/or esters to give a compound with the formula:

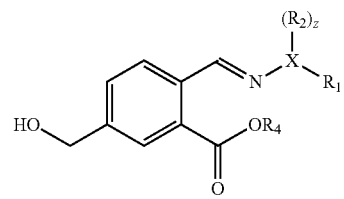

wherein $R_4$ is as defined before, and wherein the method generally further comprises oxidation of the hydroxyl to carboxylic acid.

In yet a further embodiment, the compound with formula (III) is an oxime wherein X=O, such that a hydroxylamine is used giving an oxime compound with a backbone structure having the formula (IX):

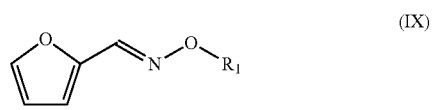

Particularly preferred as compound with formula (III) is O-benzyl hydroxylamine, that may for instance be reacted with furfural, for example using pyridine in ethanol at room temperature. Such reaction is described in *J. Org. Chem.* 73(4) 1264-1269 (2008).

For an oxime compound according to formula (IX), the dienophile may for instance be an alkyne, more preferably an alkyl propiolate, such as a $C_1$-$C_4$ alkyl propiolate, in particular methyl propiolate.

In an embodiment, methyl propiolate is reacted with furfural-benzyloxime, for instance in an organic polar solvent such as ethyl acetate, using for example a Lewis acid metal as catalyst, such as aluminium chloride. Also possible is that DFF, furfural, 5-HMF, 5-MMF, and/or chloromethylfurfural (also known as 5-chloromethylfurfural or 5-CMF) is reacted with a hydroxylamine with formula (III) and a propiolate is used as dienophile, more preferably an alkyl propiolate such as methyl propiolate.

In a preferred embodiment, the product is terephthalic acid and the dienophile is ethylene. More preferably, the compound with formula (II) is 5-hydroxymethylfurfural, 5-methoxymethylfurfural or 2,5-furandicarboxaldehyde. Preferably, the reaction of the dienophile with the compound with a backbone structure according to formula (IV) is catalysed by a Lewis and/or Brønsted acid.

In a preferred embodiment, the invention relates to a terephthalic acid production process comprising reacting a hydrazone or oxime substituted furan with ethylene under cycloaddition reaction conditions and in the presence of a catalyst to produce a bicyclic ether, dehydrating the bicyclic ether to produce a hydrazone or oxime substituted phenyl and converting the substituted phenyl to terephthalic acid. Examples of cycloaddition reaction conditions are e.g. a temperature of about 100° C. to about 300° C., an ethylene partial pressure from about 1 to about 100 bar, and/or a reactor residence time of for example more than 1 hour. The process may be performed batch-wise or in a continuous process.

Possible catalysts include activated carbon, silica, alumina, a zeolite, or a molecular sieve. For example, the catalyst may be a heterogeneous material providing Lewis and/or Brønsted acid functionality. Optionally, at least 6 of the carbon atoms of the obtained terephthalic acid are derived from one or more renewable feed stocks. Optionally, the furan is not methyl substituted when reacted with ethylene. Preferably, the furan is substituted at the 2 position with a hydrazone or oxime functionality when reacted with ethylene.

Yet a further embodiment relates to a process of preparing a hydrazone and/or oxime substituted phenylic compound, comprising reacting a hydrazone and/or oxime substituted furanic compound, preferably substituted with hydrazone or oxime at the 2 position, and preferably obtained from renewable feedstock, with a non-substituted and/or unactivated alkyne or alkene compound, in particular acetylene or ethylene, under cycloaddition reaction conditions, followed by or further comprising dehydration of the adduct to give a phenylic compound. The phenylic compound may be reacted further for instance to a carboxylic acid or to 1,4 cyclohexane dimethanol. Preferred features of such process are as for the preparation of benzene carboxylic acids.

Yet a further preferred method comprises reacting 5-HMF to 2,5-furandicarboxaldehyde (DFF), reacting DFF with a hydrazine or hydroxylamine compound according to formula (III), wherein X is preferably N and preferably $R_2$ and $R_1$ are both methyl, and the compound according to formula (III) with ethylene as dienophile to give a hydrazone or oxime benzaldehyde compound. The benzaldehyde compound can usually be reacted further to terephthalic acid or 4-hydroxybenzoic acid, such as by hydrolysis and oxidation. The method may also start with reacting DFF with hydrazine or the oxime compound.

In yet a further embodiment, 5-HMF is directly reacted with a hydrazine or oxime compound according to formula (III), wherein X is preferably N and preferably $R_2$ and $R_1$ are both methyl, to give a hydrazone or oxime benzyl alcohol compound, that can be converted to terephthalic acid or 4-hydoxybenzoic acid, preferably terephthalic acid, by relatively mild hydrolysis and oxidation. If instead of ethylene, acetylene is used, 2-hydroxyterephthalic acid, 2-hydroxy-isophtalic acid, 2,4-dihydroxybenzoic acid or 3,4-dihydroxybenzoic acid may be obtained.

The invention also relates to the use of hydrazone or oxime substituted furan compounds for the preparation of phenylic compounds by the reaction with ethylene or acetylene. This reaction gives a hydrazone or oxime substituted phenylic compound, that may for instance be useful as precursor or intermediate for the preparation of compounds such as monomers for various polymers, in particular polycarbonates or polyesters, such as polyesters having monomers or co-monomers comprising an aromatic ring, such as polyethylene-terephthalate.

The invention also relates to the use of hydrazine or hydroxylamine compounds for the activation of biomass derived compounds for Diels Alder reactions, in particular for reaction of biomass derived dienes with ethylene or acetylene. Optionally, this use involves solid-supported hydrazone or hydroxylamine compounds, and a heterogeneous solid material comprising hydrazine and/or hydroxylamine groups is contacted with biomass derived compounds, in particular furfural carbaldehyde compounds.

In an aspect, the invention also relates to use of hydrazine and/or hydroxylamine compounds that are preferably solid-supported, for the activation of furanic compounds in an effluent of the preferably catalytic dehydration of carbohydrates, preferably without intermediate reduction of the furanic compounds, for reaction of the furanic compound with a dienophile to give aromatic compounds. Preferably the effluent is a liquid stream obtained from a reactor for the dehydration of carbohydrate. Preferably, the carbohydrate dehydration and the reaction with the hydrazine and/or hydroxylamine are carried out simultaneously in separate zones of a continuous process.

In some embodiments, the method is for the preparation of an ester having a backbone structure according to formula (Ia):

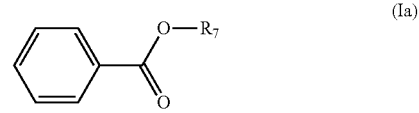

wherein $R_7$ is an optionally substituted and/or heteroatom containing hydrocarbyl group. $R_7$ can for example be selected from the group of $C_1$-$C_{20}$ linear or branched alkyl, alkenyl, alkynyl, cycloalkyl, aryl, aralkyl and alkaryl, optionally containing heteroatoms and/or substituents for example selected from the group consisting of F, Cl, Br, I, —$CH_2F$, —$CH_2Cl$, —$CH_2Br$, —$CH_2I$, —CN, —$NO_2$, —CHO, —$CO_2H$ and esters thereof, —$CH_2NH_2$ and secondary, tertiary and quaternary amines or amides thereof, and —$CH_2OH$ and esters or ethers thereof; wherein said heteroatoms are optionally selected from O, N, S, and P. Generally, the corresponding amides can also be obtained as product.

The method suitably comprises converting the compound with a backbone structure according to formula (V) into an ester, preferably by hydrolysis and oxidation. Preferably, the method comprises in situ hydrolysis and esterification of the compound with a backbone structure according to formula (V).

More generally, the hydrolysis and oxidation may involve the formation of a hemiacetal and oxidation of the hemiacetal, optionally followed by hydrolysis of the ester to the corresponding carboxylic acid, for instance through a saponification procedure.

Some illustrative non-limiting reaction schemes of aspects of the invention are shown below.

Scheme 3 - Preparation of phenol and/or benzoic acid from furfural with ethylene

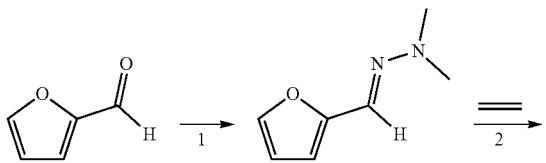

Scheme 1 - Preparation of terephthalic acid from 5-HMF with ethylene via two alternative pathways 4a or 4b.

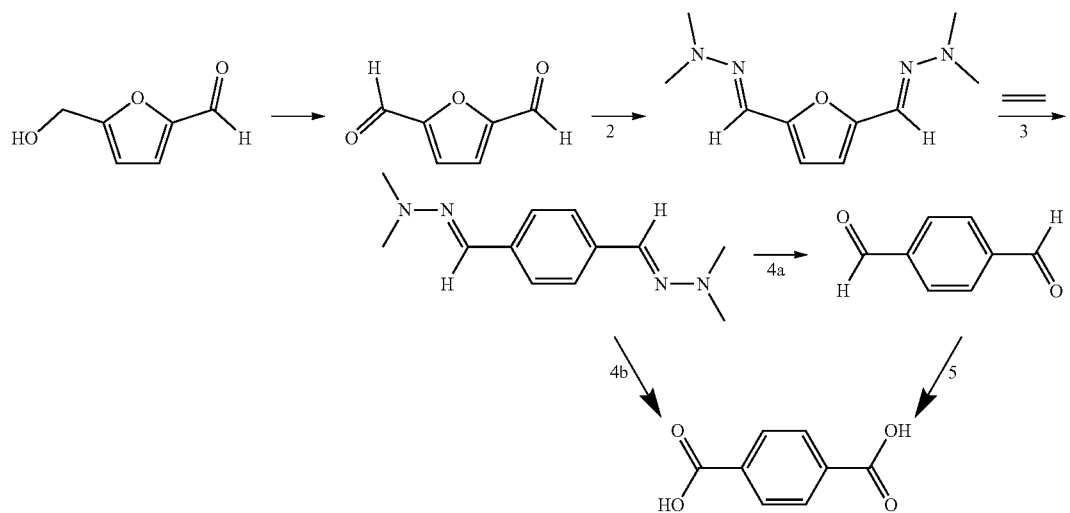

Scheme 2 - Preparation of terephthalic acid from 5-HMF with ethylene via two alternative pathways 3a,4a or 3b,4b.

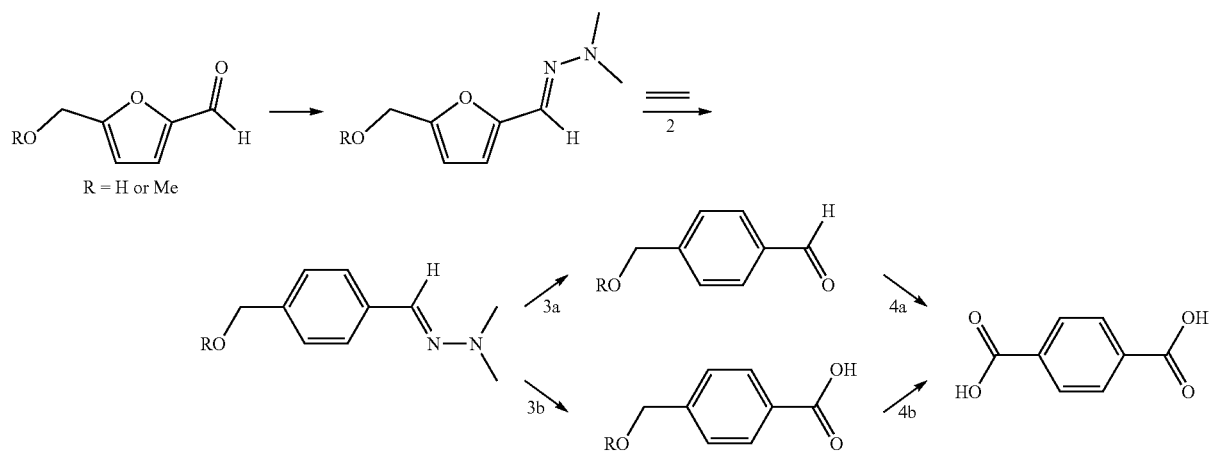

-continued

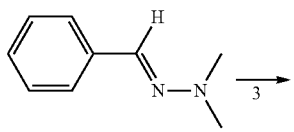

-continued
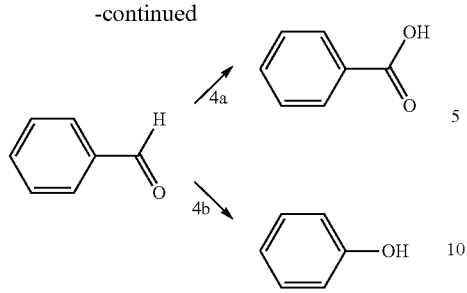
Scheme 4 - Preparation of isophthalic acid and/or phthalic acid from furfural with methyl acrylate via two alternative pathways 3a,4 or 3b.
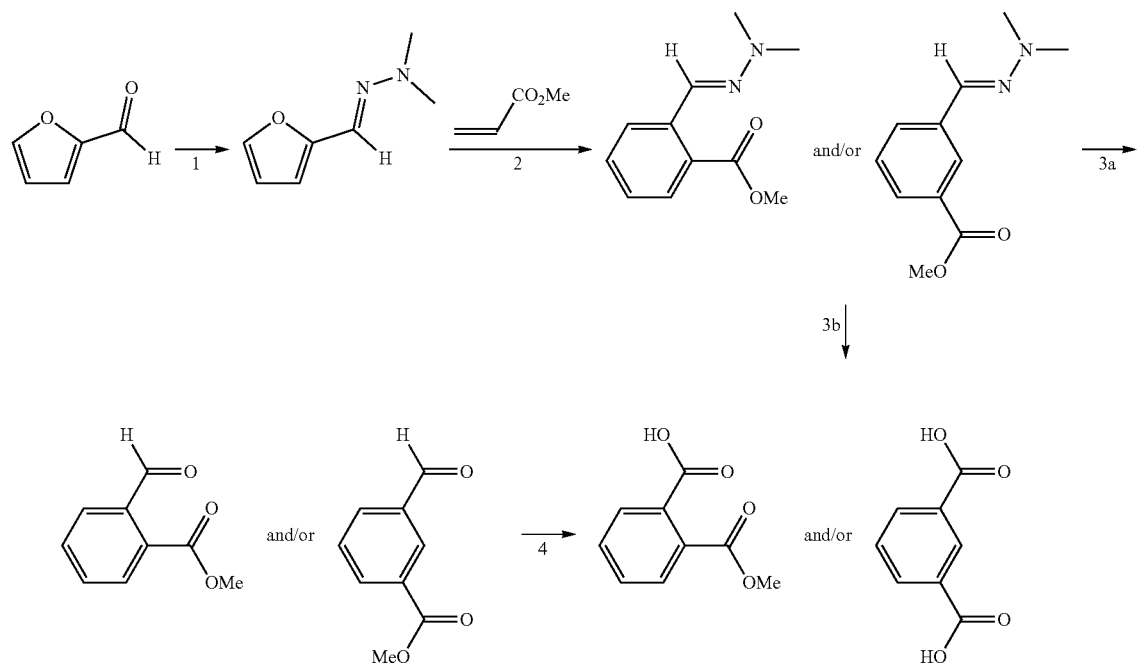
Scheme 5 - Preparation of hemi-mellitic acid from furfural with maleic anhydride via two alternative pathways 3a,4 or 3b.
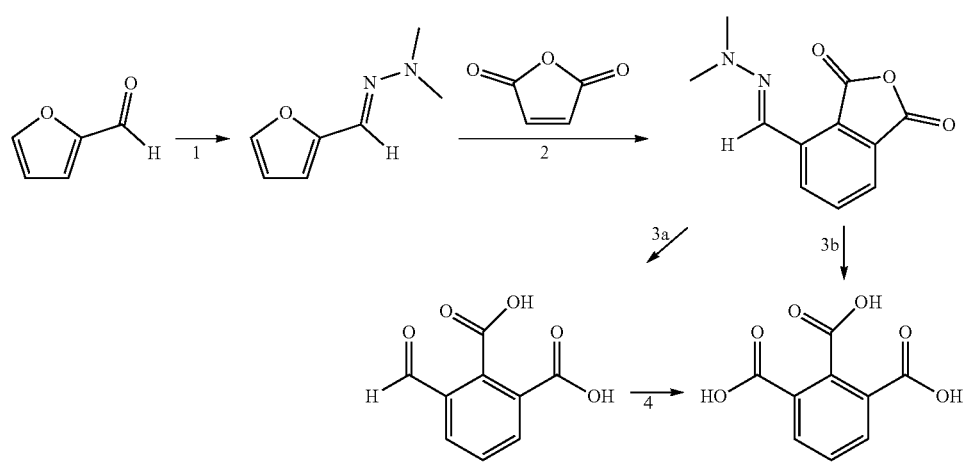

Scheme 6 - Preparation of trimellitic acid from 5-HMF with methyl acrylate via two alternative pathways 4a, 5 or 4b.

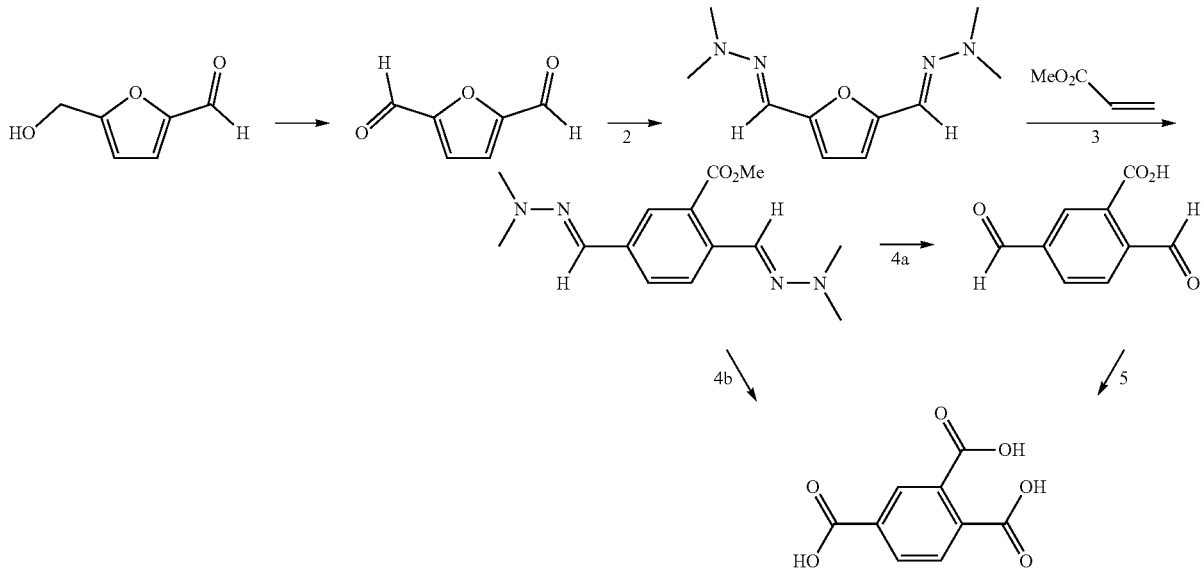

Optionally, a combination of hydrazone and oxime can be used. Optionally, a combination of an alkene and alkyne dienophile may be used. Any references to mechanisms and intermediate are included without wishing to be bound by way of theory.

As used herein, with "backbone structure" is meant that the formula schematically represents a core structure of a group of compounds, which are optionally additionally substituted with any group or atom at any position. Moreover, the backbone structures include at least any regioisomers and/or diastereomers, such as, for example, cis/trans isomers. Any references to compounds with formula (I), (II), (IV) and (V) are to backbone structures optionally having substituents, even if not expressly recited. Any reference to hydrocarbyl substituents includes heteroatom containing hydrocarbyl substituents, such as hydrocarbyl groups containing for example one or more atoms selected from the group of O, N, S and P, for example a substituent selected from the group consisting of alkyl, aryl, alkenyl, alkynyl, cycloalkyl, aralkyl and alkaryl, optionally containing heteroatoms.

EXAMPLES

The invention will now be further illustrated by the following non-limiting examples of various steps of the methods of the invention.

Example 1

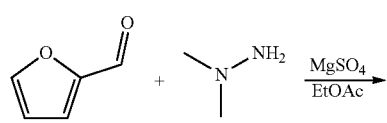

-continued

To a reactor was added magnesium sulfate (14.44 g, 1 eq.) and ethyl acetate (58.6 mL), and the mixture was stirred. To this was added furfural (11.53 g, 9.94 mL, 1 equivalents (eq.), and after 2 minutes 1,1-dimethylhydrazine (7.284 g, 9.22 mL, 1.01 eq.) was then added dropwise, and the reaction was stirred at room temperature for 16 hours. The reaction mixture was filtered to remove the solids, then the cake was washed with ethyl acetate (2×20 mL). To the resulting yellow solution of furfural-dimethylhydrazone was added maleic anhydride (15.00 g) and ethyl acetate (30 mL), and the mixture was stirred vigorously. After 3 minutes, trifluoroacetic acid (684 mg, 459 µL) was added, and the reaction was heated to 60° C. and held for 3 hours. The reaction mixture was cooled to 0° C. and stirred for 20 minutes, then the formed solid was isolated by vacuum filtration. The filtrate appeared to contain product. The cake was washed with ice-cold EtOAc (2×30 mL), then dried in a vacuum oven to yield a bright yellow solid (18.5 g, yield 71% over 2-steps).

In a variation, the reaction could be stirred for about 3 hours. Magnesium sulfate is suitable not required for a good yield of hydrazone and is optionally omitted. A wide variety of solvents were found to be suitable for the formation of the hydrazone. The Diels-Alder reaction can also be performed in a range of solvents. The reaction can be catalyzed by a range of acid catalysts. The Diels-Alder reaction proceeds without TFA, but slower. The Diels-Alder was also observed to proceed at ambient temperature. Further results indicate that the reaction can be telescoped even when the solvent is wet from the first reaction. For example, a one-pot synthesis with reagents added to a reactor sequentially and without work-up can be used. The reaction mixture was darker in color than with dry solvent for the DA reaction, but the reaction is quite clean by HPLC.

Example 2

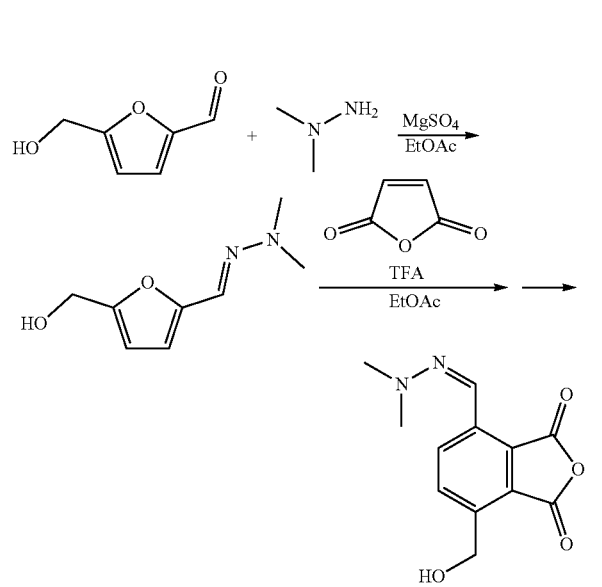

To a reactor was added magnesium sulfate (7.37 g, 1 eq.) and ethyl acetate (29.9 mL), and the mixture was stirred. To this was added HMF (7.718 g, 1 eq.), and after 2 minutes 1,1-dimethylhydrazine (3.715 g, 4.702 mL, 1.01 eq.) was then added dropwise, and the reaction was stirred at room temperature for 16 hours (3 hours is expected to be sufficient). The reaction mixture was filtered to remove the solids, then the cake was washed with ethyl acetate (2×20 mL). To the resulting orange solution of HMF-dimethylhydrazone was added maleic anhydride (7.652 g, 1.275 eq.) and ethyl acetate (30 mL), and the mixture was stirred vigorously. After 3 minutes, trifluoroacetic acid (349 mg, 234 µL, 0.05 eq.) was added, and the reaction was heated to 60° C. and held for 1 hour. The reaction mixture was cooled to ambient temperature then washed with saturated sodium bicarbonate solution (30 mL), then water. The resulting organic solution was dried over sodium sulfate, filtered and reduced to yield and oil. This was purified over silica, eluting with ethyl acetate/heptane. The appropriate fractions were collected and reduced to yield the desired product as an orange oil (1.975 g, 13% over 2-steps).

Example 3

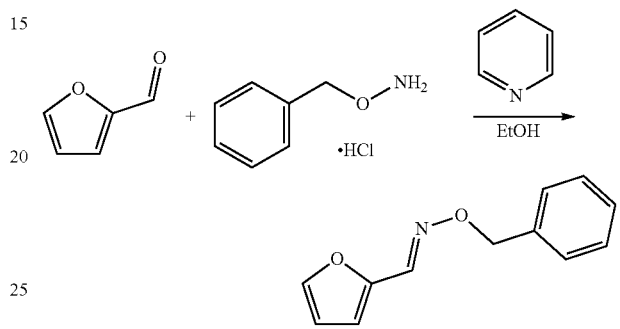

To a reactor was added O-benzylhydroxylamine hydrochloride (766 mg, 1.2 eq.) and absolute ethanol (3 mL), and the mixture was stirred vigorously, then pyridine (1.264 g, 1.293 mL, 4 eq.) was added dropwise. To this was added furfural (384 mg, 331 µL, 1 eq.) dropwise. This was stirred at room temperature for 4 hours (the reaction is expected to be complete in minutes, e.g. less than 15 minutes), then the ethanol was removed by rotary evaporation to yield a white solid and light yellow liquid. To this dissolved/suspended in dichloromethane (15 mL), and the mixture extracted twice with a 5% citric acid solution (30 mL). The combined aqueous was back extracted with dichloromethane (15 mL) and the combined organics dried over sodium sulfate, filtered, and reduced to yield a light-yellow oil. This was then purified on over silica eluting with an n-Hexane:EtOAc solvent system. Appropriate fractions were collected and reduced to yield the desired product as a clear oil (719 mg, 103%).

Example 4

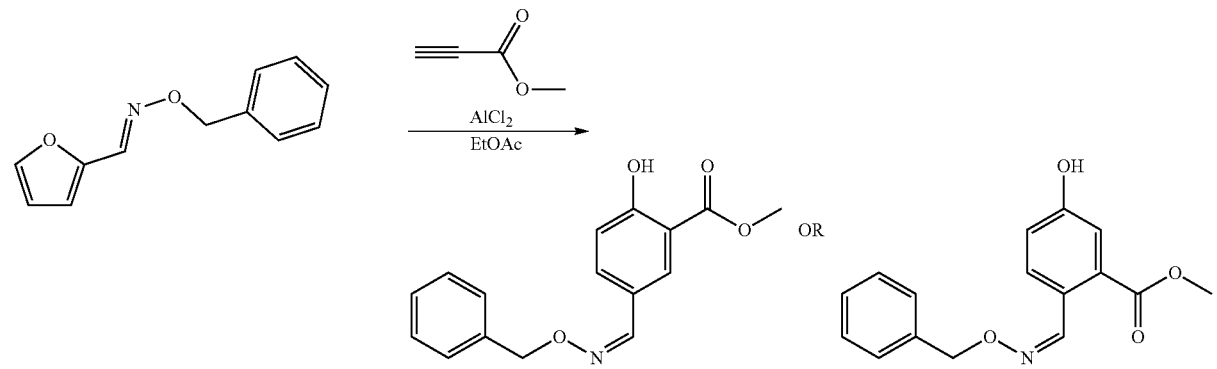

To a reactor was charged methyl propiolate (26.6 mg, 28.2 μL, 1.275 eq.) and ethyl acetate (100 μL), and stirring was started. To this was added a solution of the furfural-benzyloxime (50 mg, 1 eq.) in ethyl acetate (100 μL) dropwise over 5 mins. The reaction mixture was cooled to 0° C. and then aluminium chloride (40 mg) was added. The cooling was removed and the reaction allowed to warm to room temperature and stirred for 1 hour. The reaction mixture was cooled to 0° C. then quenched by the dropwise addition of water (2 mL). Ethyl acetate (2 mL) was added and the organics were separated. The aqueous was extracted with a second portion of ethyl acetate (5 mL). The combined organics were washed with water, dried over sodium sulfate, filtered and reduced to an oil by rotary evaporation. Purified over silica eluting with an n-Hexane:EtOAc solvent system. Appropriate fractions were collected and reduced to yield the desired product as brown oil (5 mg, 7%).

Example 5

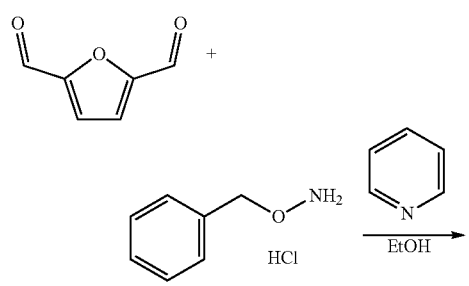

-continued

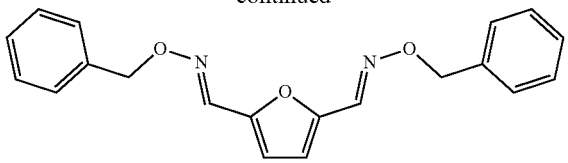

To a reactor was added O-benzylhydroxylamine hydrochloride (766 mg, 1.2 eq.) and absolute ethanol (3 mL), and the mixture was stirred vigorously, then pyridine (1.264 g, 1.293 mL, 4 eq.) was added dropwise. To this was added 2,5-furandicarboxaldehyde (248 mg, 1 eq.) dropwise. This was stirred at room temperature for 4 h (the reaction is expected to be complete in minutes, e.g. less than 15 minutes). Then the ethanol was removed by rotary evaporation to yield a white solid and light yellow liquid. To this dissolved/suspended in dichloromethane (15 mL), and the mixture extracted twice with a 5% citric acid solution (30 mL). The combined aqueous was back extracted with dichloromethane (15 mL) and the combined organics dried over sodium sulfate, filtered, and reduced to yield a light yellow oil. This was then purified over silica eluting with an n-Hexane:EtOAc solvent system. Appropriate fractions were collected and reduced to yield the desired product as a light yellow oil (646 mg, 97%).

Example 6

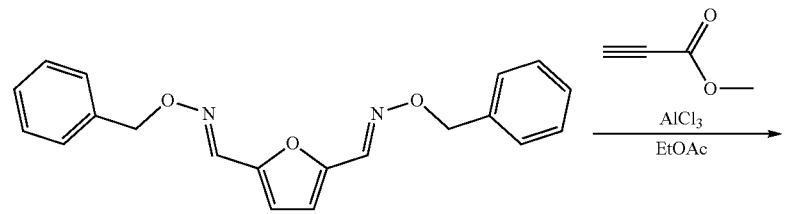

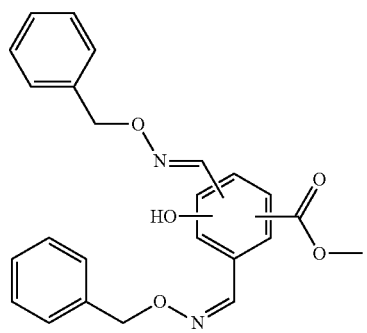

To a reactor was charged methyl propiolate (32.0 mg, 33.9 µL, 1.275 eq.) and ethyl acetate (250 µL), and stirring was started. To this was added a solution of the 2,5-furandicarboxaldehyde-bis-benzyloxime (100 mg, 1 eq.) in ethyl acetate (250 µL) dropwise over 5 mins. The reaction mixture was cooled to 0° C., then aluminium chloride (100 mg, 2 eq.) was added. The cooling was removed and the reaction allowed to warm to room temperature and stir for 1 hour. The reaction mixture was cooled to 0° C. then quenched by the dropwise addition of water (2 mL). Ethyl acetate (2 mL) was added and the organics were separated. The aqueous was extracted with a second portion of ethyl acetate (5 mL). The combined organics were washed with water, dried over sodium sulfate, filtered and reduced to an oil by rotary evaporation. Purified over silica eluting with an n-Hexane: EtOAc solvent system. Appropriate fractions were collected and reduced to yield 3 separate region-isomers of the desired product:

Product 1 isolated as a yellow oil (25 mg, 20%).
Product 2 isolated as a yellow oil (20 mg, 16%).
Product 3 isolated as a brown oil (15 mg, 12%).
Overall yield=60 mg, 48%.

Example 7

To a reactor was charged 3-formylphthalic anhydride-dimethylhydrazone (2.5 g, 1 eq.) and 10% aqueous nitric acid (25 mL), and this was heated to 100° C. with vigorous stirring. After ~30 minutes, when all of the solid had dissolved and no more gas was given off, the reactor was configured to distill water. The reaction mixture was reduced to ~10 mL in volume, then cooled to around 75° C. The surface of the reactor was scratched with a pipette to induce crystallization. The solid which formed was isolated by filtration. The cake was washed with ice-cold water (2×10 mL), then dried in a vacuum oven to yield a cream colored solid (1.97 g; 89%). The product is possibly hemi-mellitic anhydride.

Example 8

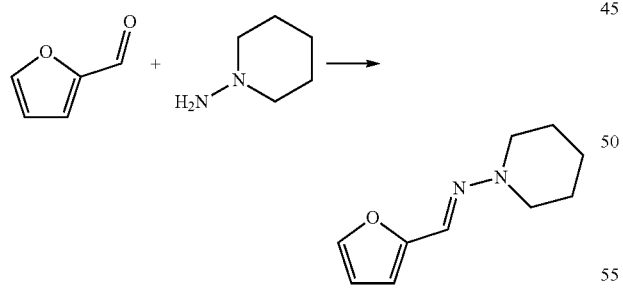

To a reactor was charged N-aminopiperidine (5.26 g, 5.67 mL), and toluene (25 mL), and the mixture was stirred vigorously. To this was added furfural (5.00 g, 4.31 mL) dropwise. This was stirred at room temperature for 2 minutes then heated to reflux under Dean-Stark conditions. This was maintained until no more water was observed to collect in the Dean-Stark trap (~40 minutes). The reaction mixture was the reduced by rotary evaporation to yield a red/brown oil. NMR analysis confirmed this as the desired product (9.23 g, 99%).

Example 9

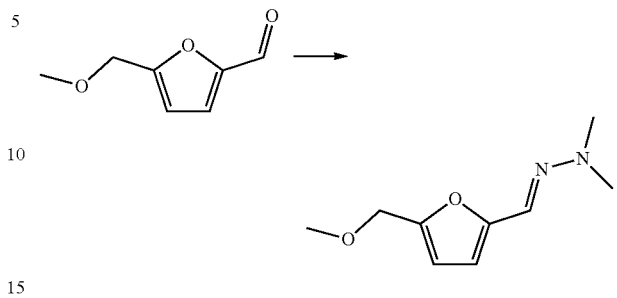

To a reactor was charged 1,1-dimethylhydrazine (3.715 g, 4.702 mL), magnesium sulfate (7.37 g) and ethyl acetate (29.9 mL), and the mixture was stirred vigorously. To this was added 5-methoxymethylfurfural (8.577 g) dropwise. This was stirred at room temperature for 16 h then the reaction mixture was filtered and the cake washed with ethyl acetate (2×50 mL). The filtrate was reduced by rotary evaporation to yield an orange oil. NMR analysis confirmed this as the desired product (11.0 g, 99%).

Example 10

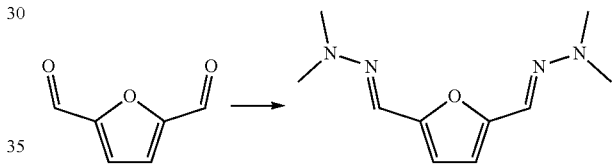

To a reactor was charged 1,1-dimethylhydrazine (553 mg, 700 µL), magnesium sulfate (2.407 g) and dichloromethane (3 mL), and the mixture was stirred vigorously. To this was added 2,5-furandicarboxaldehyde (248 mg) dropwise. This was stirred at room temperature for 5 h then the reaction mixture was filtered and the cake washed with DCM (2×10 mL). The filtrate was reduced by rotary evaporation to yield a yellow oil. NMR analysis confirmed this as the desired product (402 mg, 97%).

Example 11

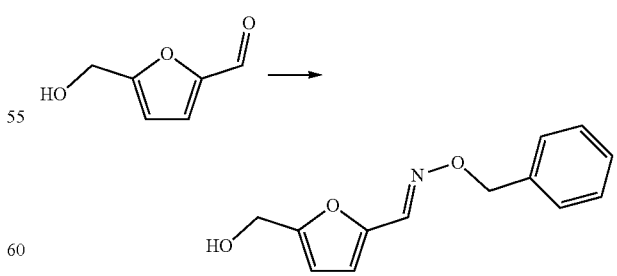

To a reactor was charged O-benzylhydroxylamine hydrochloride (766 mg) and absolute ethanol (3 mL), and the mixture was stirred vigorously. To this was added pyridine (1.264 g, 1.293 mL) dropwise, quickly. To this was added 5-hydroxymethylfurfural (504 mg) dropwise. This was stirred at room temperature for 4 h then the ethanol was removed by rotary evaporation. This dissolved in dichloromethane (15 mL), and the mixture extracted twice with a 5% citric acid solution (30 mL). The combined aqueous was back extracted with dichloromethane (15 mL) and the combined organics dried ($Na_2SO_4$), filtered, and reduced to yield a clear oil. NMR analysis confirmed this as the desired product (803 mg, 87%) as a mixture of regio-isomers.

Example 12

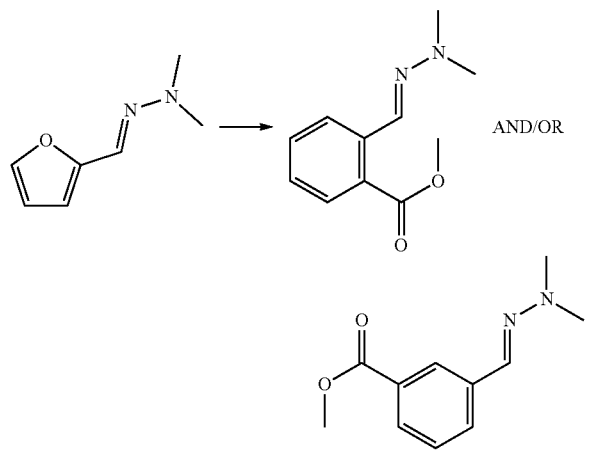

AND/OR

To a reactor was charged the above furfural hydrazone (1.382 g), hydroquinone (2 mg) and methyl acrylate (861 mg, 906 µL). The tube was sealed and the mixture heated to 200° C. in a microwave, with stirring, and held for 3 hours. The reaction mixture was cooled to 20° C., then purified by flash chromatography. Appropriate fractions were collected and reduced to yield a yellow oil. NMR analysis confirmed this as the meta-isomer of the desired product (1.05 g, 51%). Trace amounts of the ortho-isomer (~100 mg impure) were also isolated.

Example 13

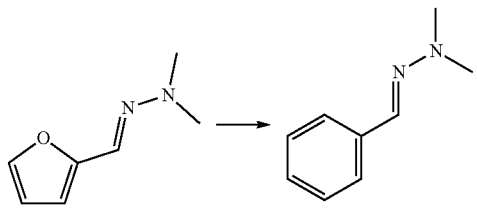

To a reactor was charged the above furfural hydrazone (415 mg), copper triflate (5 mg) and 1,4-dioxane (5.75 mL), and the solution was stirred and bubbled through with nitrogen gas. The reactor was then sealed and brought to 35 bar of pressure with ethylene gas. The mixture was then heated to 250° C., with vigorous stirring, and held for 7 hours. The reactor was cooled to room temperature, the pressure was released, and the system flushed with nitrogen gas. The resulting mixture was reduced to an oil by rotary evaporation, and purified by flash chromatography. Appropriate fractions collected and reduced to yield a yellow oil. NMR analysis confirmed this as the desired product (98 mg, 22%).

Example 14

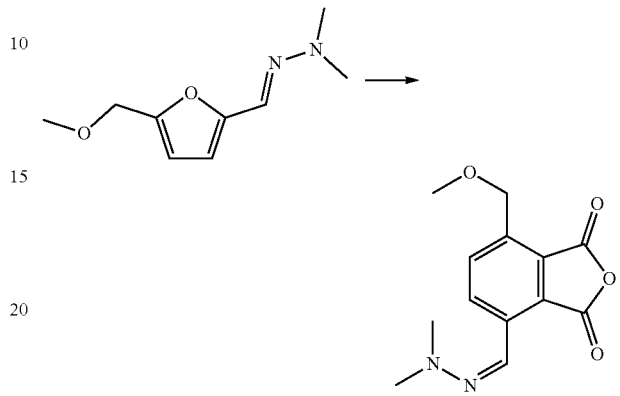

To a reactor was charged maleic anhydride (0.50 g) and ethyl acetate (2.54 mL) and this mixture was heated to 60° C. with vigorous stirring until the maleic anhydride dissolved. To this was added the hydrazone (0.729 g) in ethyl acetate (2.54 mL). The reaction was stirred at 60° C. for 150 minutes then at 20° C. for 40 hours. Reduced to an oil by rotary evaporation, and purified by flash chromatography. Appropriate fractions collected and reduced to yield a yellow solid. NMR analysis confirmed this as the desired product (430 mg, 41%).

Example 15

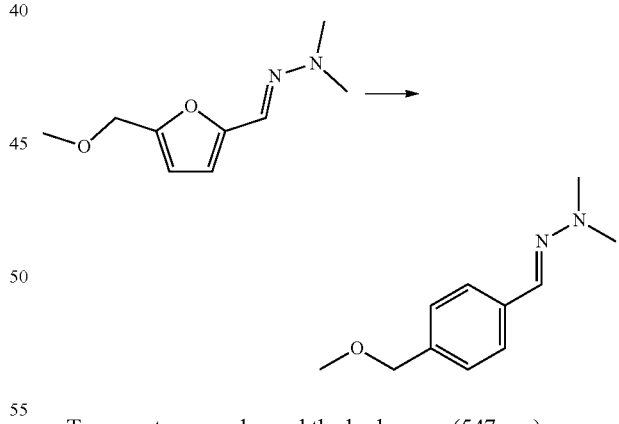

To a reactor was charged the hydrazone (547 mg), copper triflate (5 mg) and 1,4-dioxane (5.75 mL), and the solution was stirred and bubbled through with nitrogen gas. The reactor was then sealed and brought to 35 bar of pressure with ethylene gas. The mixture was then heated to 250° C., with vigorous stirring, and held for 7 hours. The reactor was cooled to room temperature, the pressure was released, and the system flushed with nitrogen gas. The resulting mixture was reduced to an oil by rotary evaporation, and purified by flash chromatography. Appropriate fractions collected and reduced to yield a yellow oil. NMR analysis confirmed this as the desired product (98 mg, 17%).

Example 16

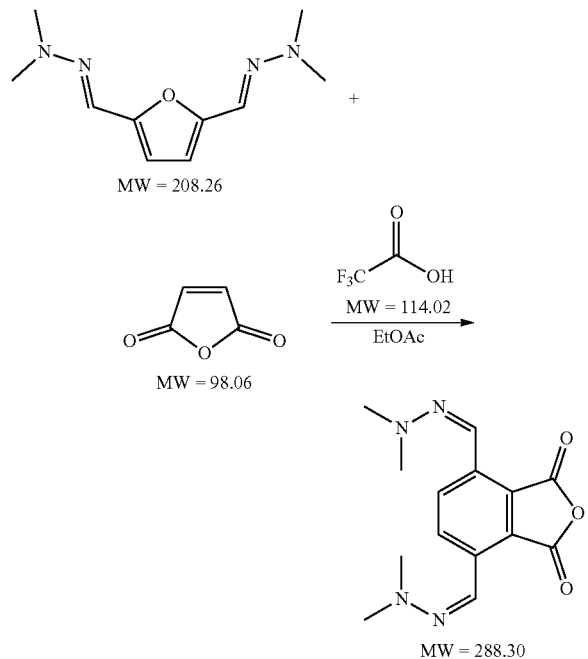

To a reactor was charged maleic anhydride (37.4 mg) and ethyl acetate (225 mg, 250 μL), and the mixture was stirred vigorously. To this was added a solution of the hydrazone (62.5 mg) in ethyl acetate (225 mg, 250 μL) dropwise over 2 mins. The reaction immediately became bright orange in colour. Trifluoroacetic acid (1.7 mg, 1.1 μL) was then added, the tube was stoppered tightly and the reaction was stirred at room temperature for 40 hours. Reduced by rotary evaporation then purified by flash chromatography. Appropriate fractions collected and reduced to yield a brown solid. NMR analysis confirmed this as the desired product (95 mg, 98%) as a mixture of regio-isomers.

Example 17

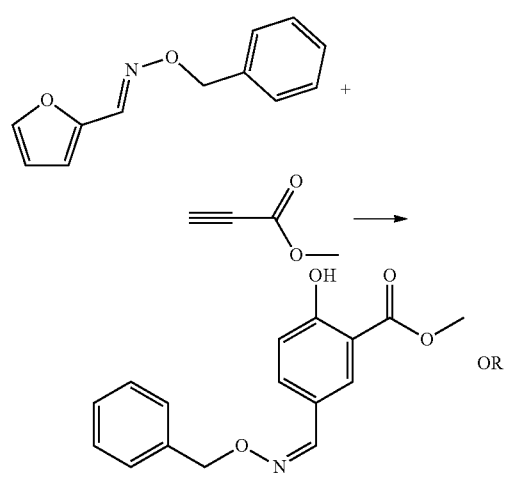

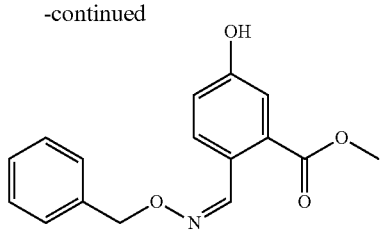

To a reactor was added methyl propiolate (26.6 mg, 28.2 μL) and ethyl acetate (90.2 mg, 100 μL), and the mixture was stirred vigorously. To this was added a solution of furfural-oxime (50 mg) in ethyl acetate (90.2 mg, 100 μL) dropwise over 5 mins. This was stirred for 5 minutes then the reaction was cooled to 0° C., then aluminium chloride (40 mg) was added. The cooling was removed and the reaction allowed to warm to room temperature. The mixture was cooled to 0° C. then quenched by the dropwise addition of ice-water (2 mL). Ethyl acetate (2 mL) was added and the organics were separated and the aqueous extracted with a second portion of ethyl acetate (5 mL). The combined organics were washed with water, dried ($Na_2SO_4$), filtered and reduced to an oil by rotary evaporation. Purified by flash chromatography. Appropriate fractions collected and reduced to yield a yellow oil. NMR analysis confirmed this as the desired product (55 mg, 78%) as a mixture of regio-isomers.

Example 18

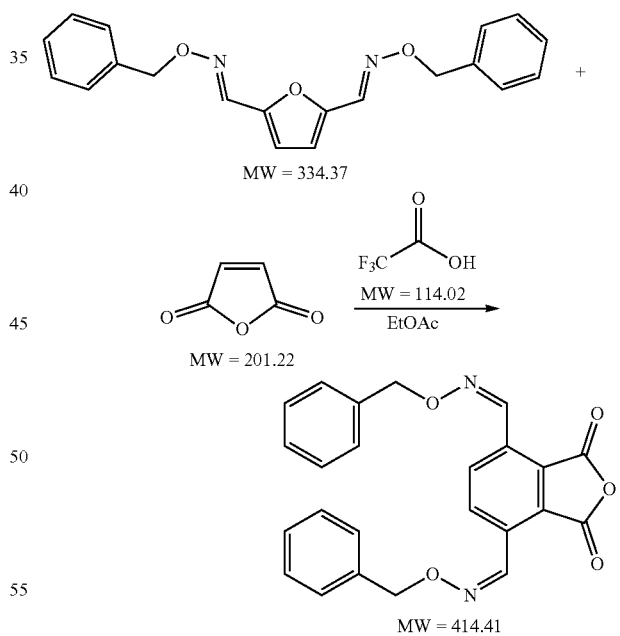

To a reactor was charged maleic anhydride (37.4 mg) and ethyl acetate (225 mg, 250 μL), and the mixture was stirred vigorously. To this was added a solution of DFF-Oxime (100 mg) in ethyl acetate (225 mg, 250 μL) dropwise over 2 mins. This was stirred for 5 minutes then the reaction was cooled to 0° C., then aluminium chloride (40 mg) was added. The cooling was removed and the reaction allowed to warm to room temperature. The mixture was cooled to 0° C. then quenched by the dropwise addition of ice-water (2 mL).

Ethyl acetate (2 mL) was added and the organics were separated and the aqueous extracted with a second portion of ethyl acetate (5 mL). The combined organics were washed with water, dried (Na₂SO₄), filtered and reduced to an oil by rotary evaporation. Purified by flash chromatography. Appropriate fractions collected and reduced to yield a yellow oil. NMR analysis confirmed this as the desired product (25 mg, 20%) as a mixture of regio-isomers.

Example 19

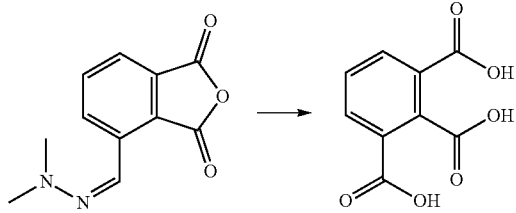 [SMILES: CN(C)/N=C\c1cccc2c1C(=O)OC2=O ; O=C(O)c1cccc(C(=O)O)c1C(=O)O]

To a reactor was charged a 10% solution of nitric acid in water (1200 mL), and this was heated to 95° C. with stirring. Furfural unsymmetrical dimethylhydrazine (UDH) hydrazone-maleic anhydride Diels-Alder (DA) product (150 g) was then added slowly and portionwise, limited by NO₂ evolution, over ~60 minutes. The reaction mixture was cooled 0° C., and the solid which precipitate was isolated by filtration and washed with ice-cold water (20 mL). The resulting solid was dried in a vacuum oven at 30° C. overnight to yield a white solid. NMR analysis confirmed this as the desired product (75 g, 52%). The filtrates were reduced to around ⅕ of their original volume by rotary evaporation, then were cooled 0° C., and the solid which precipitate was isolated by filtration and washed with ice-cold water (5 mL). The resulting solid was dried in a vacuum oven at 30° C. overnight to yield a white solid. NMR analysis confirmed this as the desired product (17 g, 52%).

Example 20

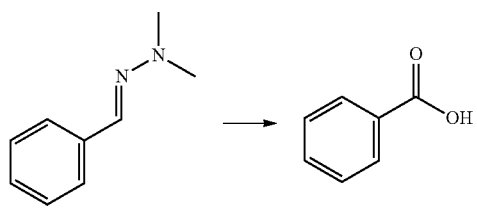

To a reactor was charged a 10% solution of nitric acid in water (500 μL), and the above benzaldehyde hydrazone (100 mg), and this was heated to 95° C. with stirring for 30 minutes. The reaction mixture was cooled to 20° C., and the organics were extracted with dichloromethane (2×2 mL). The combined organics were dried (Na₂SO₄), filtered and educed by evaporation to yield a white solid. NMR analysis confirmed this as benzoic acid (68 mg, 82%).

Example 21

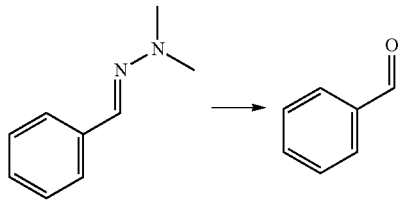

To a reactor was charged a 10% solution of sulfuric acid in water (5000 μL), toluene (500 μL) and the above benzaldehyde hydrazone (100 mg), and this was heated to 110° C. with stirring in a microwave for 20 minutes. The reaction mixture was cooled to 20° C., and the organic phase was separated. The aqueous phase was extracted with toluene (500 μL), and the combined organics were dried (Na₂SO₄), filtered and carefully reduced by evaporation to yield a clear liquid. NMR analysis confirmed this as benzaldehyde (62 mg, 86%).

Example 22

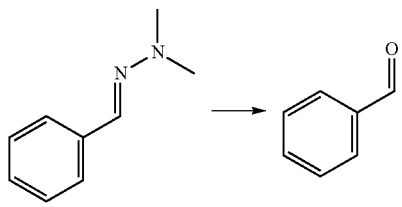

To a reactor was charged a 10% solution of hydrochloric acid in water (500 μL), toluene (500 μL) and the above benzaldehyde hydrazone (100 mg), and this was heated to 110° C. with stirring in a microwave for 20 minutes. The reaction mixture was cooled to 20° C., and the organic phase was separated. The aqueous phase was extracted with toluene (500 μL), and the combined organics were dried (Na₂SO₄), filtered and carefully reduced by evaporation to yield a clear liquid. NMR analysis confirmed this as benzaldehyde (56 mg, 78%).

Example 23

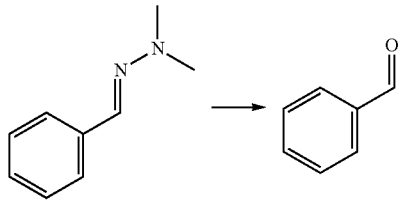

To a reactor was charged a 10% solution of phosphoric acid in water (500 μL), toluene (500 μL) and the above benzaldehyde hydrazone (100 mg), and this was heated to 110° C. with stirring in a microwave for 20 minutes. The reaction mixture was cooled to 20° C., and the organic phase was separated. The aqueous phase was extracted with toluene (500 µL), and the combined organics were dried (Na$_2$SO$_4$), filtered and carefully reduced by evaporation to yield a clear liquid. NMR analysis confirmed this as benzaldehyde (50 mg, 71%).

Example 24

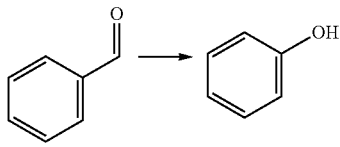 [SMILES: O=Cc1ccccc1 ; Oc1ccccc1]

To a reactor was charged boric acid (3.1 g), 30% hydrogen peroxide (2.5 g), and tetrahydrofuran (30 mL). This was stirred vigorously, then concentrated sulfuric acid (1 mL) was added dropwise. This was stirred at room temperature for 30 minutes, then a solution of benzaldehyde (1.06 g) in tetrahydrofuran (10 mL) was added dropwise. The reaction mixture was stirred at room temperature. The reaction mixture was filtered and the solid washed with tetrahydrofuran (5 mL). the combined filtrates were neutralized with aqueous saturated sodium hydrogen carbonate solution and was extracted with dichloromethane (2×40 mL). The organic phase was dried (Na$_2$SO$_4$), filtered and reduced to yield a white solid. NMR analysis confirmed this as the desired product (780 mg, 83%).

Example 25

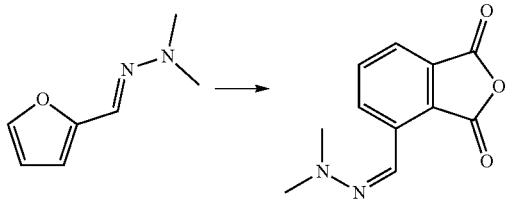

Several reaction conditions were screened for the effect on the above Diels-Alder reaction of furfural unsymmetrical dimethyl hydrazone (1 eq.) and maleic anhydride (1 eq. unless indicated otherwise).

The reaction was investigated with various solvents (concentration of 1.8 mol/L hydrazone) at 60° C., in the absence of a catalyst. The various solvents are 2-methyltetrahydrofuran (2-MTHF), acetone, acetic acid, anisole (PhOMe), cyclohexane, dichloromethane (DCM), dimethyl carbonate (DMC) 1,4-dioxane (dioxane), dimethylformamide, dimethylsulfoxide, ethyl acetate (EtOAc), ethanol, acetonitrile, nitromethane, methyl acetate (MeOAc), methylisobutylketone (MIBK), methyl t-butylether (MTBE), chlorobenzene, benzonitrile (PhCN), triethylamine, 2,2,2-trifluoroethanol, trifluoroacetic acid and toluene. The results for the 8 best solvents are shown in FIG. 1.

Figure 2:
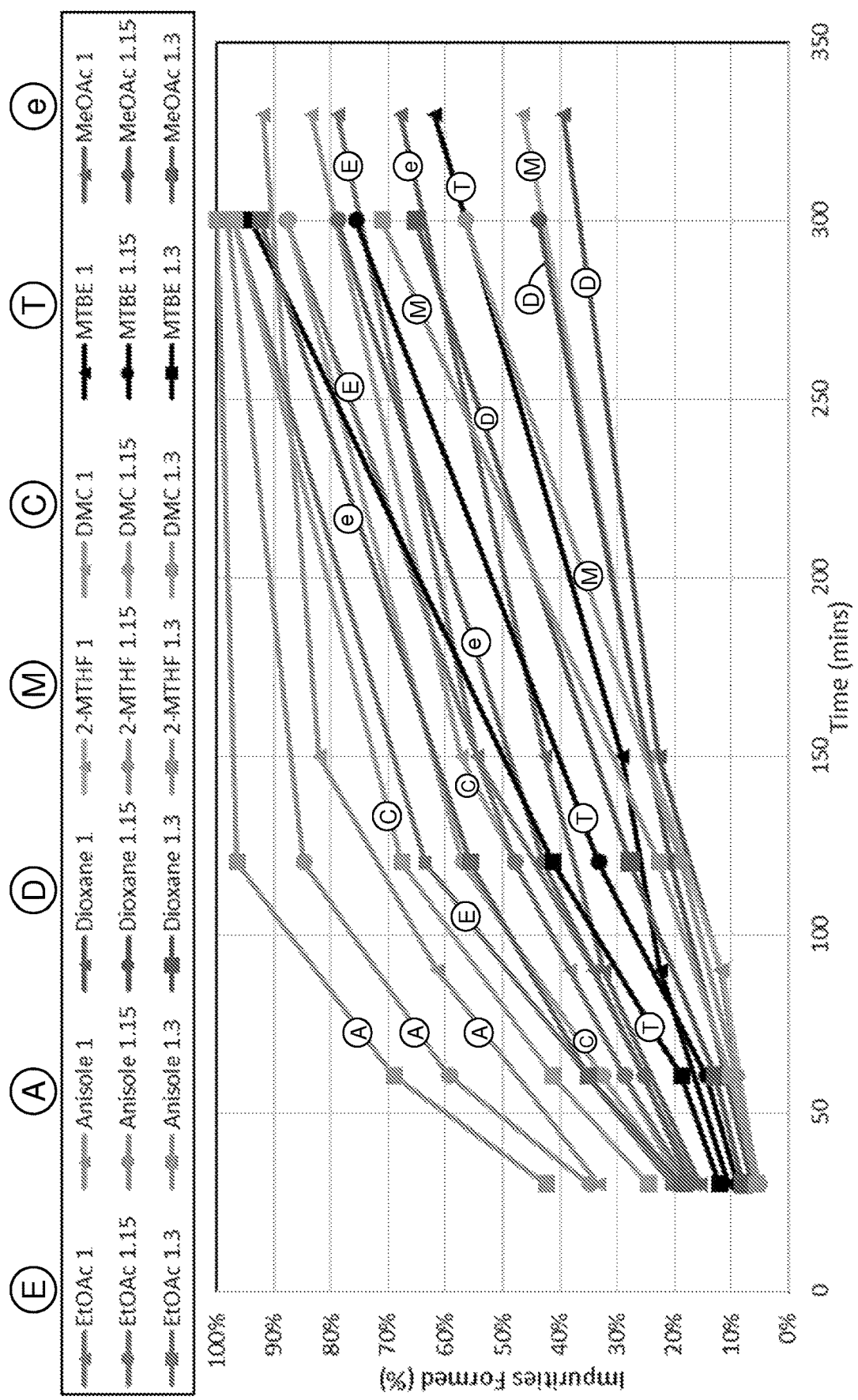
FIG. 2 is line graph of the peak to peak conversion in time for the best solvents from FIG. 1 using varying amounts of maleic anhydride (1 equivalent, 1.15 equivalents, and 1.3 equivalents, with a concentration of 1.8 mol/L hydrazone) at 60° C., in the absence of a catalyst.

A selection of the best solvents were then subjected to reaction with varying amounts of maleic anhydride (1 equivalent, 1.15 equivalents, and 1.3 equivalents, with a concentration of 1.8 mol/L hydrazone) at 60° C., in the absence of a catalyst. The results, peak-to-peak conversion in time, are shown in FIG. 2.

Figure 3:
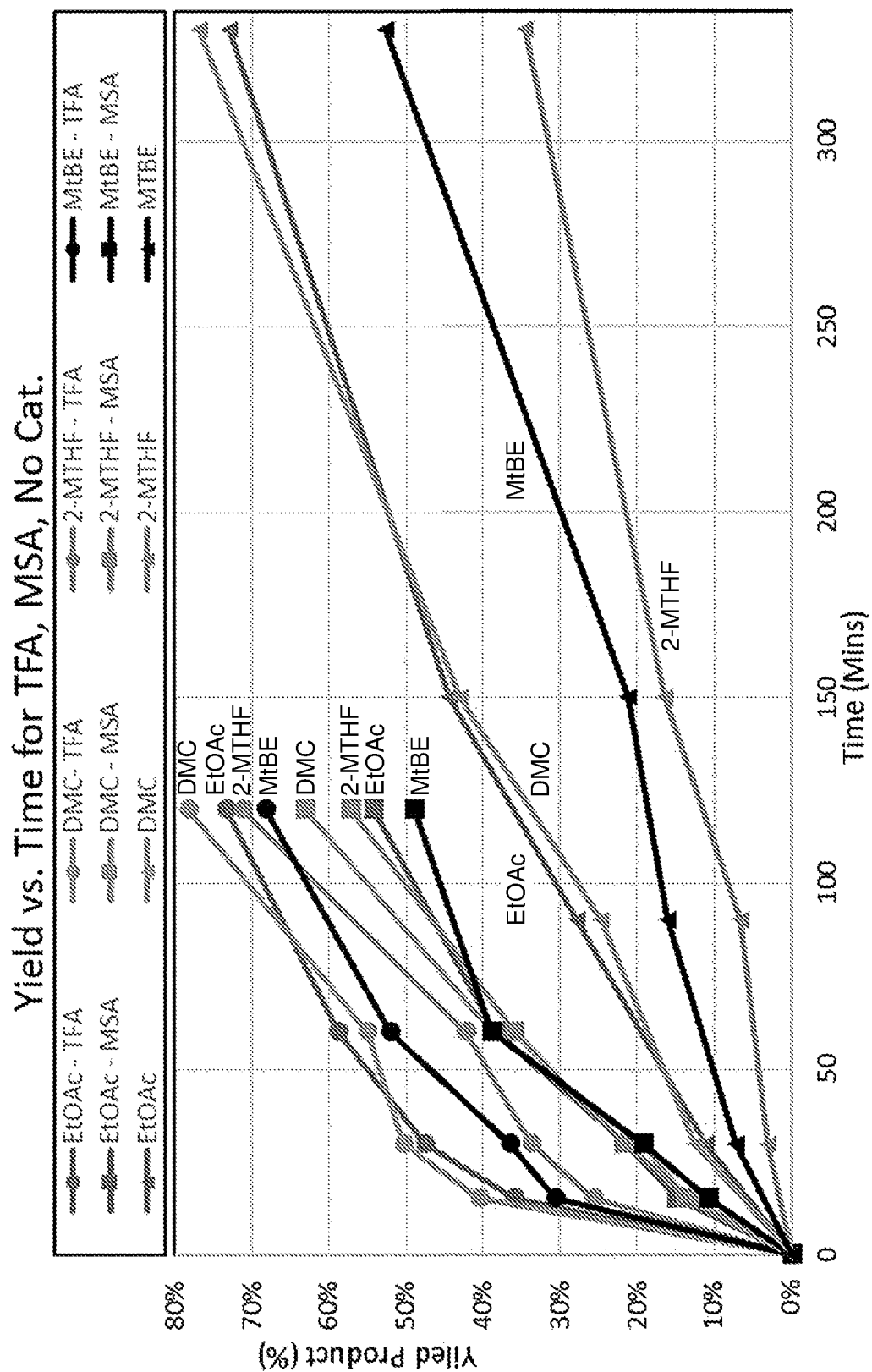
FIG. 3 is line graph of the peak to peak conversion in time for the best solvents from FIG. 1 using varying catalysts (0.05 equivalent, with a concentration of 1.8 mol/L hydrazone) at 60° C., with 1 equivalent on maleic anhydride.

A selection of the best solvents were then subjected to reaction with varying catalysts (0.05 equivalent, with a concentration of 1.8 mol/L hydrazone) at 60° C., with 1 equivalent on maleic anhydride. The various catalysts are trifluoroacetic acid (TFA), methanesulfonic acid (MSA), tetrafluoroboric acid diethyl ether complex (BF4/ether), trifluoromethanesulfonic acid (TfOH), para-toluenesulfonic acid (pTSA), Amberlyst resin, sulfuric acid (H$_2$SO$_4$), formic acid and acetic acid. The results for the best 3 scenarios are shown in FIG. 3.

Example 26

Furfural-Dibenzyl-Hydrazone Synthesis

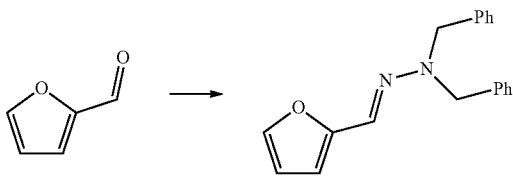 [SMILES: O=Cc1ccco1 ; C(=N\N(Cc1ccccc1)Cc1ccccc1)/c1ccco1]

To a reactor was charged 1,1-dibenzylhydrazine (10.7 g), magnesium sulfate (6.13 g) and ethyl acetate (24.8 ml), and the mixture was stirred vigorously. To this was added furfural (4.84 g, 4.18 ml) dropwise. This was heated to 60° C. with stirring for 2 h then the reaction mixture was filtered while hot. The filtrate was slowly cooled to 0° C. with stirring, allowing for a solid to form. This was isolated by filtration, and washed with ice-cold ethyl acetate (10 ml). The resulting solid was dried in a vacuum oven at 35° C. to yield a light yellow solid. NMR analysis confirmed this as the desired product (12.5 g, 85%).

Example 27

Furfural-Piperidyl-Hydrazone Synthesis

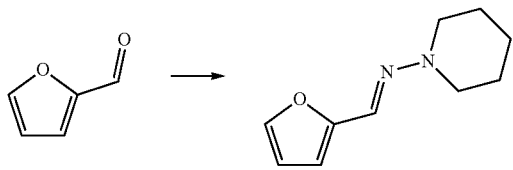 [SMILES: O=Cc1ccco1 ; C(=N\N1CCCCC1)/c1ccco1]

To a reactor was charged N-amino-piperidene (241 mg, 260 µL), magnesium sulfate (290 mg) and ethyl acetate (1.2 ml), and the mixture was stirred vigorously. To this was added furfural (232 mg, 200 µl) dropwise. This was heated to 60° C. with stirring for 1.5 h then the reaction mixture was filtered. The resulting solution was used crude in the following reaction.

Example 28

Furfural-Phenyl-Methyl-Hydrazone Synthesis

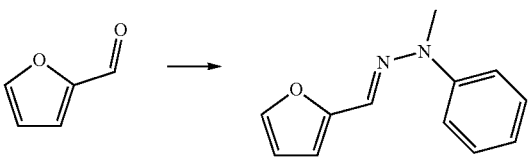

To a reactor was charged 1-methyl-1-phenylhydrazine (294 mg, 284 µL), magnesium sulfate (289 mg) and ethyl acetate (1.2 ml), and the mixture was stirred vigorously. To this was added furfural (232 mg, 200 µl) dropwise. This was heated to 60° C. with stirring for 1.5 h then the reaction mixture was filtered. The resulting solution was used crude in the following reaction.

Example 29

Furfural-Dibenzyl-Hydrazone/Maleic Anhydride Diels Alder:

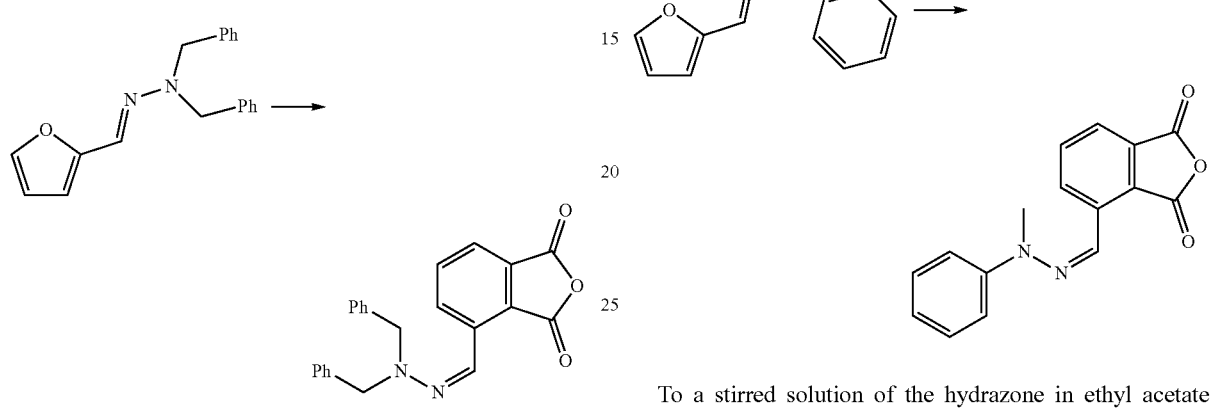

To a reactor was charged furfural-dibenzyl-hydrazone (700 mg) and ethyl acetate (1.2 ml), and this was heated to 60° C. with stirring to obtain solution. A solution of maleic anhydride (295 mg, 1.25 molar equivalents) in ethyl acetate (1.9 ml) was then charged, followed by trifluoroacetic acid (14 mg, 9 µL), and the mixture was heated to 60° C. and held for 1 hour. Analysis by LCMS showed 100% conversion to the desired aromatic hydrazone. Aternatively, no trifluoracetic acid was added, and the reaction heated at 60° C. for 6 hours, then analysis should 100% conversion to desired aromatic.

Example 30

Furfural-Dibenzyl-Hydrazone/Maleic Anhydride Diels Alder:

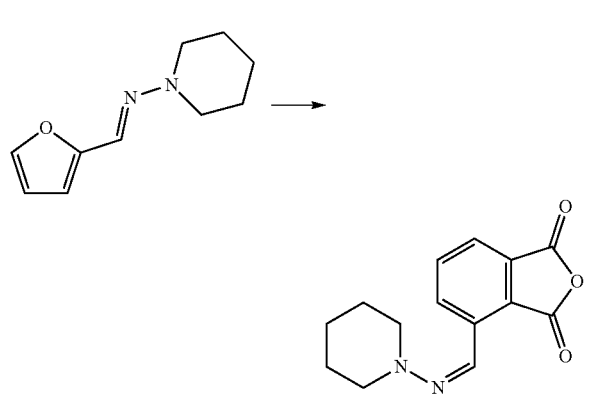

To a stirred solution of the hydrazone in ethyl acetate (prepared previously), was added a solution of maleic anhydride (295 mg, 1.25 molar equivalents) in ethyl acetate (1.9 ml), followed by trifluoroacetic acid (14 mg, 9 µL), and the mixture was heated to 60° C. and held for 3 hours. Analysis by LCMS showed 100% conversion to the desired aromatic hydrazone.

Example 31

Furfural-Dibenzyl-Hydrazone/Maleic Anhydride Diels Alder:

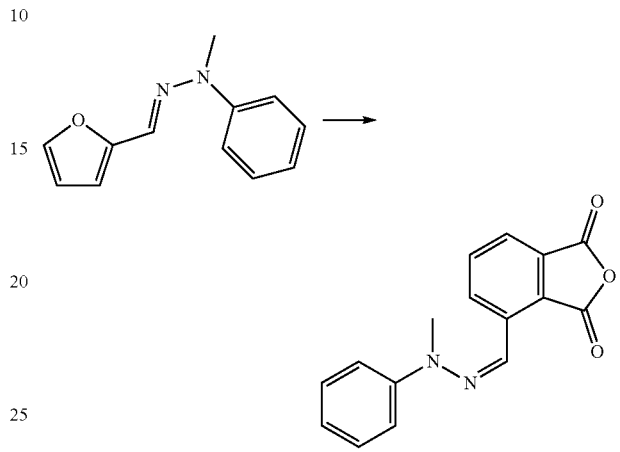

To a stirred solution of the hydrazone in ethyl acetate (prepared previously), was added a solution of maleic anhydride (295 mg, 1.25 molar equivalents) in ethyl acetate (1.9 ml), followed by trifluoroacetic acid (14 mg, 9 µL), and the mixture was heated to 60° C. and held for 6 hours. Analysis by LCMS showed 46% conversion to the desired aromatic hydrazone.

Example 31

Hydrolysis/oxidation of Furfural-UDH-Hydrazone-Maleic Anhydride DA Product (with 65% HNO3):

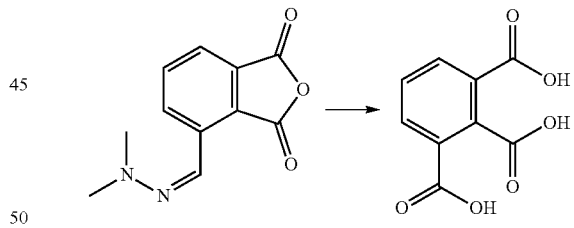

To a reactor was charged a 65% solution of nitric acid (150 mL). The stirring was started vigorously and the reactor was heated to 95° C. A flow of nitrogen was applied across the flask, and vented a scrubber containing sodium hydroxide solution. Furfural unsymmetrical dimethylhydrazine (UDH) hydrazone-maleic anhydride Diels-Alder (DA) product (150 g) was then added in portions over ~60 minutes. 5 minutes after complete addition, 65% nitric acid was added dropwise until no further gas evolution was observed. Water (150 ml) was then added and the reaction mixture was allowed to cool slowly to 20° C., then was cooled to 0° C., and the solid which precipitate was isolated by filtration and washed with ice-cold water (20 mL). The resulting solid was dried in a vacuum oven at 30° C. overnight to yield a white solid. NMR analysis confirmed this as the desired product (110 g, 76%). The filtrates were reduced to around ½ of their original volume by rotary evaporation, then were cooled 0° C., and the solid which precipitate was isolated by filtration and washed with ice-cold water (5 mL). The resulting solid was dried in a vacuum oven at 30° C. overnight to yield a white solid. NMR analysis confirmed this as the desired product (17 g, 12%).

Example 32

MMF-Hydrazone/Maleic Anhydride Diels Alder:

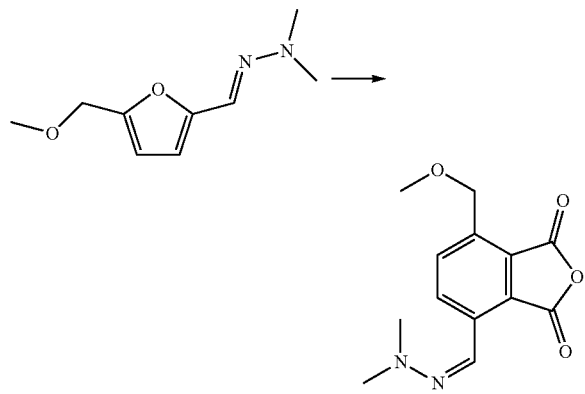

Several reaction conditions were screened for the effect on the above Diels-Alder reaction of MMF-unsymmetrical dimethyl hydrazone (1 eq.) and maleic anhydride (1 eq.).

Figure 4:
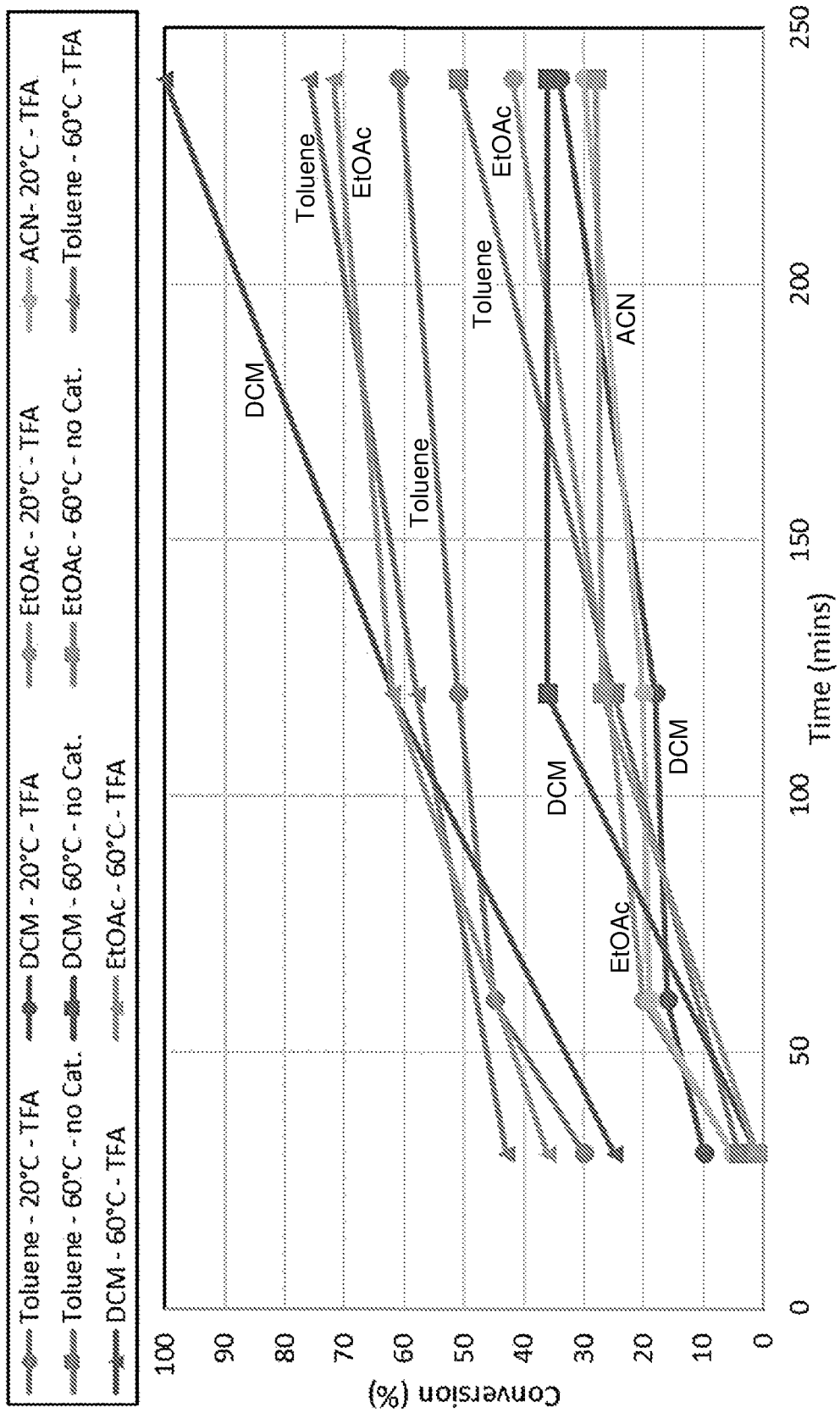
FIG. 4 is line graph of the peak to peak conversion in time for the reaction of Example 32 using varied reaction conditions: various solvents (concentration of 0.7 mol/L hydrazone) at 20° C. with catalysis by TFA, and at 60° C. both in the presence and absence of TFA as catalyst, for a period of 4 hours. The various solvents are dichloromethane (DCM), ethyl acetate (EtOAc), acetonitrile, and toluene.

The reaction was investigated with various solvents (concentration of 0.7 mol/L hydrazone) at 20° C. with catalysis by TFA, and at 60° C. both in the presence and absence of TFA as catalyst, for a period of 4 hours. The various solvents are dichloromethane (DCM), ethyl acetate (EtOAc), acetonitrile, and toluene. The results are shown in FIG. 4.

Example 33

Furfural-UDH-Hydrazone/1,1,1,3,3,3-Hexfluoroisopropyl Acrylate Diels Alder:

To a reactor was charged furfural-UDH-Hydrazone (387 μL), hydroquinone (4 mg), 1,1,1,3,3,3-hexfluoroisopropyl acrylate (488 μL), and toluene (2 ml). The tube was sealed and the mixture heated to 190° C. in a microwave, with stirring, and held for 3 hours. The reaction mixture was analysed by HPLC, showing the meta-isomer of the product to be present as the major product in around 60% yield, with furfural-UDH-Hydrazone the predominant other component. A minor peak for the ortho-isomer is also present.

Example 34

Furfural-UDH-Hydrazone/1,1,1,3,3,3-Hexfluoroisopropyl Acrylate Diels Alder:

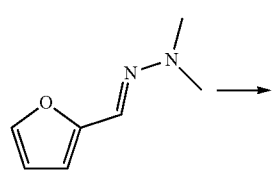

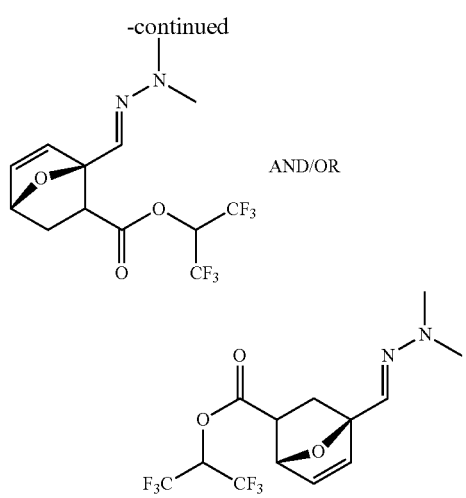

AND/OR

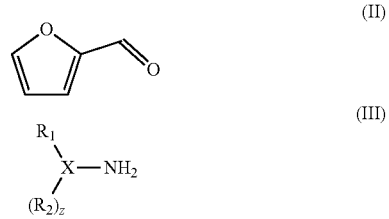

To a reactor was charged 2-methyl-CBS-oxazaborolidine (24 mg) and DCM (1 ml) and the stirring was started. Trifluoromethanesulfonic acid (6 μL) was then added and the mixture was stirred for 30 minutes at room temperature. To this was added 1,1,1,3,3,3-hexfluoroisopropyl acrylate (165 μL), followed by furfural-UDH-Hydrazone (330 μL). The reaction was stirred at room temperature for 4 hours. The reaction mixture was analysed by NMR, showing the reaction to have proceeded to yield the desired products. The yield was not determined.

The invention claimed is:

1. A method of preparing an optionally substituted compound comprising formula (I):

wherein:
G is OH CHO, or $CO_2H$, an ether thereof, an ester thereof, or an anhydride thereof, the method comprising:
(i) reacting a biomass-derived compound comprising formula (II) with a compound comprising formula (III):

(II)

(III)

wherein:
the compound of formula (II) is optionally substituted at one or more of the 3, 4, or 5 position with a $C_1$-$C_{20}$ hydrocarbyl or with F, Cl, Br, I, $CH_2F$, $CH_2Cl$, $CH_2Br$, $CH_2I$, CN, $NO_2$, CHO, $CO_2H$ or ester thereof, $CH_2NH_2$ or secondary, tertiary, or quaternary amine or amide thereof, or $CH_2OH$ or ester or ether thereof; wherein said $C_1$-$C_{20}$ hydrocarbyl is optionally substituted is one or more of F, Cl, Br, I, CH$_2$F, CH$_2$Cl, CH$_2$Br, CH$_2$I, CN, NO, CHO, CO$_2$H or ester thereof, CH$_2$NH$_2$ or secondary, tertiary, or quaternary amine or amide thereof, or CH$_2$OH or ester or ether thereof;

X is O and z is 0, or

X is N and z is 1,

R$_1$ is a C$_1$-C$_{20}$ hydrocarbyl, optionally substituted with one or more phenyl, F, Cl, Br, I, CH$_2$F, CH$_2$Cl, CH$_2$Br, CH$_2$I, CN, NO$_2$, CHO, CO$_2$H or ester thereof, CH$_2$NH$_2$ or secondary, tertiary, or quaternary amine or amide thereof, or CH$_2$OH or ester or ether thereof, and R$_2$ is hydrogen or a C$_1$-C$_{20}$ hydrocarbyl, optionally substituted with one or more phenyl, F, Cl, Br, I, CH$_2$F, CH$_2$Cl, CH$_2$Br, CH$_2$I, CN, NO$_2$, CHO, CO$_2$H or ester thereof, CH$_2$NH$_2$ or secondary, tertiary, quaternary amine or amide thereof, or CH$_2$OH or ester or ether thereof, to give an optionally substituted compound comprising formula (IV):

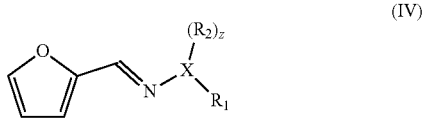

(IV)

(ii) reacting the optionally substituted compound comprising formula (IV) with a C$_2$-C$_{12}$ alkene or C$_2$-C$_{12}$ alkyne in the presence of a Lewis and/or Brønsted acid catalyst to give an optionally substituted compound comprising formula (V):

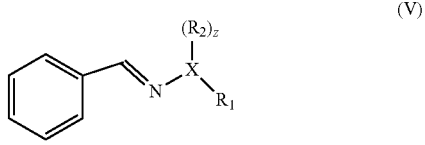

(V)

(iii) hydrolyzing said optionally substituted compound comprising formula (V) to yield the optionally substituted compound comprising formula (I), wherein G is CHO, and (iv-a) optionally decarbonylating the product of step (iii) to provide the optionally substituted compound comprising formula (I), wherein G is OH, or (iv-b) optionally oxidizing the product of step (iii) to yield the optionally substituted compound comprising formula (I), wherein G is CO$_2$H, and (v) optionally converting the optionally substituted compound comprising formula (I), wherein G is OH, CHO, or CO$_2$H to the ether, ester, or anhydride thereof.

2. The method according to claim 1, wherein said optionally substituted compound comprising formula (II) is furfural, furan-2,5-dicarbaldehyde, methoxymethylfurfural, chloromethylfurfural, 5-hydroxymethylfurfural, or a mixture thereof.

3. The method according to claim 1, wherein the optionally substituted compound comprising formula (I) is a phenol, a hydroxyl benzene tricarboxylic acid, a hydroxyl benzene dicarboxylic acid, a hydroxyl benzene carboxylic acid, a benzene dicarboxylic acid, a benzene tricarboxylic acid, or a benzene tetracarboxylic acid, or an ester, ether or anhydride thereof.

4. The method according to claim 1, wherein step (ii) is performed using ethylene.

5. The method according to claim 4, wherein the optionally substituted compound comprising formula (II) is 5-hydroxymethylfurfural, 5-methoxymethylfurfural, 5-chloromethylfurfural or 2,5-furandicarboxaldehyde, and the optionally substituted compound comprising formula (I) is terephthalic acid.

6. The method according to claim 5, wherein step (ii) further comprises a catalyst that is a Brønsted acid and/or a Lewis acid supported on a solid material.

7. The method according to claim 5, wherein the optionally substituted compound comprising formula (II) is furfural and the optionally substituted compound comprising formula (I) is phenol or an ester thereof.

8. The method according to claim 1, wherein step (ii) performed using C$_2$-C$_{12}$ alkyne.

9. The method according to claim 8, wherein the optionally substituted compound comprising formula (III) is a hydroxylamine, wherein X is O.

10. The method according to claim 9, wherein step (ii) is performed using a propiolate and the optionally substituted compound comprising formula (II) is 2,5-furandicarboxaldehyde, furfural, 5-hydroxymethylfurfural, 5-methoxymethylfurfural, 5-chloromethylfurfural, or a combination thereof.

11. The method according to claim 1, wherein step (ii) is performed using acrylic acid or an acrylate ester.

12. The method according to claim 1, further comprising hydrolyzing and oxidizing the optionally substituted compound comprising formula (V) to an optionally substituted ester comprising formula (Ia):

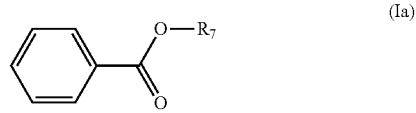

(Ia)

wherein, R$_7$ is a heteroatom-containing C$_1$-C$_{20}$ hydrocarbyl group that is optionally substituted with one or more phenyl, F, Cl, Br, I, CH$_2$F, CH$_2$Cl, CH$_2$Br, CH$_2$I, CN, NO, CHO, CO$_2$H or ester thereof, CH$_2$NH$_2$ or secondary, tertiary, quaternary amine or amide thereof, or CH$_2$OH or ester or ether thereof.

13. The method according to claim 1, wherein the optionally substituted compound comprising formula (III) is provided on a heterogeneous solid support, and the method further comprises recovering the optionally substituted compound comprising formula (III) by separating solid material comprising the optionally substituted compound comprising formula (III) from a liquid phase comprising an optionally substituted aromatic compound comprising formula (I).

14. The method according to claim 1, wherein the optionally substituted compound comprising formula (II) is an effluent from a reactor for the (catalytic) dehydration of carbohydrates, wherein the effluent comprises water or an organic solvent.

15. The method according to claim 1, wherein step (ii) is performed using maleic anhydride and the optionally substituted compound comprising formula (V) is converted into the optionally substituted compound comprising formula (I) in a single step comprising hydrolysis step (iii) and oxidation step (iv-b).

16. A method of preparing an aromatic compound, comprising:

activating a furanic compound in an effluent from a catalytic dehydration of carbohydrates using a solid-supported hydrazine compound, solid-supported hydroxylamine compound, or a combination thereof, wherein the activating is performed in the absence of reducing the furanic compound, and reacting the activated furanic compound with a $C_2$-$C_{12}$ alkene or $C_2$-$C_{12}$ alkyne in the presence of a Lewis and/or Brønsted acid catalyst.

17. The method according to claim 1, wherein step (ii) is performed using ethylene, and the compound comprising formula (I) is phenol, benzoic acid, a benzoic acid ester, or a benzoic acid ether.

18. The method according to claim 6, wherein the solid support is a heterogeneous support.

19. The method according to claim 1, wherein $R_1$, $R_2$, or both $R_1$ and $R_2$ are substituted with phenyl, F, Cl, Br, I, $CH_2F$, $CH_2Cl$, $CH_2Br$, $CH_2I$, CN, $NO_2$, CHO, $CO_2H$, an ester of $CO_2H$, $CH_2NH_2$, a secondary amine of $CH_2NH_2$, a tertiary amine of $CH_2NH_2$, a quaternary amine of $CH_2NH_2$, an amide of $CH_2NH_2$, a secondary amide of $CH_2NH_2$, a tertiary amide of $CH_2NH_2$, a quaternary amide of $CH_2NH_2$, $CH_2OH$, an ester of $CH_2OH$, or an ether of $CH_2OH$.

\* \* \* \* \*